US012740952B2

(12) United States Patent
Yang et al.

(10) Patent No.: US 12,740,952 B2
(45) Date of Patent: Sep. 22, 2026

(54) BENZENESULFONAMIDE DERIVATIVES AND METHOD FOR MODULATING LIPID RAFT

(71) Applicant: Gongwin Biopharm Co., Ltd., Taipei City (TW)

(72) Inventors: Chuan-Ching Yang, Taipei City (TW); Mao-Yuan Lin, Taipei City (TW); Shun-Chi Wu, Taipei City (TW); Chi-Chiang Tu, Taipei City (TW); Nan-Shan Zhong, Guangzhou (CN)

(73) Assignee: Gongwin Biopharm Co., Ltd., Taipei City (TW)

( * ) Notice: Subject to any disclaimer, the term of this patent is extended or adjusted under 35 U.S.C. 154(b) by 125 days.

(21) Appl. No.: 16/959,054

(22) PCT Filed: Dec. 28, 2018

(86) PCT No.: PCT/US2018/067838

§ 371 (c)(1),
(2) Date: Jun. 29, 2020

(87) PCT Pub. No.: WO2019/133797

PCT Pub. Date: Jul. 4, 2019

(65) Prior Publication Data

US 2020/0338028 A1 Oct. 29, 2020

Related U.S. Application Data

(60) Provisional application No. 62/612,028, filed on Dec. 29, 2017.

(51) Int. Cl.

| | |
|---|---|
| ***A61K 31/18*** | (2006.01) |
| ***A61K 45/06*** | (2006.01) |
| ***A61P 3/06*** | (2006.01) |
| ***A61P 35/00*** | (2006.01) |

(52) U.S. Cl.

CPC .............. *A61K 31/18* (2013.01); *A61K 45/06* (2013.01); *A61P 3/06* (2018.01); *A61P 35/00* (2018.01)

(58) Field of Classification Search

None

See application file for complete search history.

(56) References Cited

U.S. PATENT DOCUMENTS

| | | | | |
|---|---|---|---|---|
| 5,891,454 A * | 4/1999 | Wu | ...................... | A61K 9/0019 514/604 |
| 6,727,287 B2 * | 4/2004 | Wu | ...................... | A61K 47/12 514/604 |
| 2017/0172951 A1 * | 6/2017 | Yang | .................... | A61K 31/337 |

FOREIGN PATENT DOCUMENTS

| | | | |
|---|---|---|---|
| CN | 106822099 A * | 6/2017 | ........... A61K 31/375 |

OTHER PUBLICATIONS

Anonymous, CAS SciFinder English language abstract of CN 106822099 A (2107-06-13).*

* cited by examiner

*Primary Examiner* — Brian J Davis

(74) *Attorney, Agent, or Firm* — Sughrue Mion, PLLC

(57) ABSTRACT

The present disclosure relates to a benzenesulfonamide derivative which is useful to modulate lipid raft integrity of cancer cells and the use of the benzenesulfonamide derivative in prevention or treatment of diseases or conditions which can be ameliorated by change of the lipid raft integrity in a subject.

11 Claims, 21 Drawing Sheets

BENZENESULFONAMIDE DERIVATIVES AND METHOD FOR MODULATING LIPID RAFT

This application is a national stage of application filed under 35 U.S.C. § 371 of International Application No. PCT/US18/67838 filed on Dec. 28, 2018 which claims the benefit of U.S. Provisional Application 62/612,028 filed on Dec. 29, 2017. The entire contents of these applications are incorporated herein by reference in their entirety.

BACKGROUND

1. Technical Field

The present disclosure relates to a method for modulating lipid raft integrity, especially to a method for modulating lipid raft integrity by benzenesulfonamide derivatives. The present disclosure also relates to a method for preventing or treating cancer by administering the benzenesulfonamide derivatives to a subject in need thereof.

2. Description of Associated Art

Prostate cancer has been recognized as one of the most important medical difficulties in men. It eventually develops to castration-resistant prostate cancer (CRPC) when advanced prostate cancer progresses and metastasis appears in spite of medical treatment with androgen deprivation therapy. New therapeutic agents are needed in CRPC treatment since the patients currently have few treatment options. Given that prostate cancer cells can adapt to many cellular stresses, promising therapies targeting prostate cancer differently to fight against multiple adaptive mechanisms are highly required to offer alternative therapeutic options [1].

Androgen-deprivation therapy is the mainstay therapy for advanced metastatic prostate cancer; however, it ultimately progresses to CRPC. Several mechanisms have been identified to be responsible for CRPC occurrence including amplification or point mutations in an androgen receptor gene, interaction between androgen receptors and growth factors, and activation of compensatory survival signaling pathways [2-4]. The phosphoinositide 3-kinase (PI3K)/Akt signaling pathway that plays a key role in regulating cell survival and neoplastic transformation is constitutively activated in most of the CRPCs. Activation of PI3K/Akt is most frequently reported in the category of compensatory survival signaling pathways in CRPC [5-7]. Tumor suppressor PTEN (phosphatase and tensin homolog deleted on chromosome 10), which is a negative regulator of PI3K/Akt activity, is mutated or lost in 50% to 80% patients with prostate adenocarcinoma [2]. Moreover, the decreased PTEN capability and increased PI3K/Akt activity are well correlated to a high Gleason score and with advanced pathological stage disease [8]. Also, loss of PTEN expression is correlated with worse survival and shorter time on prostate cancer therapy, such as abiraterone treatment [87]. Furthermore, Akt can negatively regulate the forkhead box transcription factor FOXO3A (a tumor suppressor) through posttranslational modifications, leading to increased cytoplasmic accumulation while resulting in decreased DNA binding which ultimately induces cell survival. It has been noted in prostate tumor specimens in which profound cytoplasmic accumulation of FOXO3A was detected with an increased Gleason score [9]. Altogether, these studies suggest a key role of PI3K/Akt in CRPC progression.

Cholesterol is an essential structural constituent to maintain the integrity and fluidity in cell membranes, and is critical to synthesis of hormones, vitamin D and bile acid and to regulation of multiple cellular signaling [10, 11]. Lipid rafts, which are membrane microdomains, preferentially associate with cholesterol, saturated lipids and kinases in regulating a number of cellular signaling pathways [12, 13]. Numerous studies have demonstrated that reduction or depletion of cholesterol from plasma membranes is capable of disrupting PI3K/Akt signal transduction [14-16], suggesting the importance of membrane cholesterol content and lipid raft integrity. For example, breast and prostate cancer cells have been reported to be more abundant in lipid rafts which lead to their higher susceptibility to apoptotic stimuli caused by cholesterol depletion [17]. Also, caveolin, flotillin, ganglioside (GM1), and glycosylphosphatidylinositol (GPI)-anchored placental alkaline phosphatase (PLAP) are deemed to be lipid raft markers [57-60], and previous studies have showed the increased expression of these lipid raft markers in some cancers such as prostate cancer [57, 61-63], lung cancer [57, 64-69], pancreas cancer [70, 71], melanoma [57, 69, 72-74], kidney cancer [57, 63, 65, 69, 75], bladder cancer [76], seminoma [60], ovarian cancer [60], cervical cancer [60], breast cancer [63, 69], colon cancer [63, 77], liver cancer [32, 58], esophageal cancer [62, 63, 78, 79], oral cancer [80], tongue cancer [62], thyroid cancer [62], meningiomas [86], bile duct cancer [70], hypopharyngeal cancer [81], nasopharyngeal cancer [64, 82], gastric cancer [83, 84], or vulvar cancer [85].

Para-toluenesulfonamide (p-TSA) is a small molecule against several cancers including hepatocellular carcinoma, non-small cell lung cancer and tongue squamous cell carcinoma in both in vitro and in vivo studies [18-21]. Furthermore, it exhibits efficient anti-tumor activity against advanced hepatocellular carcinoma and non-small cell lung cancer in clinical trials through a concurrent local injection therapy [20, 21].

Herein provided is an unexpected lipid raft-modulating agent, p-TSA and derivatives thereof, and the use of these compounds in treatment of diseases susceptible to amelioration by disturbance or disruption of lipid raft integrity, especially by cholesterol depletion.

SUMMARY

The present disclosure is based, at least in part, on the discovery of a pharmaceutical composition for modulating lipid raft integrity, comprising a benzenesulfonamide derivative, and a pharmaceutically acceptable excipient thereof.

The present disclosure also provides a method for preventing or treating cancer, comprising administering the pharmaceutical composition to a subject in need thereof.

The present disclosure demonstrates the roles of lipid rafts and cholesterol contents in p-TSA-mediated redistribution and activity of several survival kinases in CRPC cells. It is shown the first time that the disturbance of cholesterol contents and alterations of lipid raft-associated Akt/mTOR/p70S6K pathways are responsible for p-TSA-induced anti-CRPC effects.

BRIEF DESCRIPTION OF THE DRAWINGS

The present disclosure can be more fully understood by reading the following detailed description of the embodiments, with reference made to the accompanying drawings, wherein:

In FIG. 5A, PC-3 and DU-145 cells were incubated in the absence or presence of 6 mM p-TSA for 2 h. After treatment, the cells were lysed in 1% Triton X-100 and fractionated by centrifugation as described in Example 4. The protein expressions were detected by Western blotting. In FIGS. 5B and 5C, the expressions were quantified using Image Lab Software 6.0 (BIO-RAD).

DETAILED DESCRIPTION OF THE EMBODIMENTS

Figure 1A:
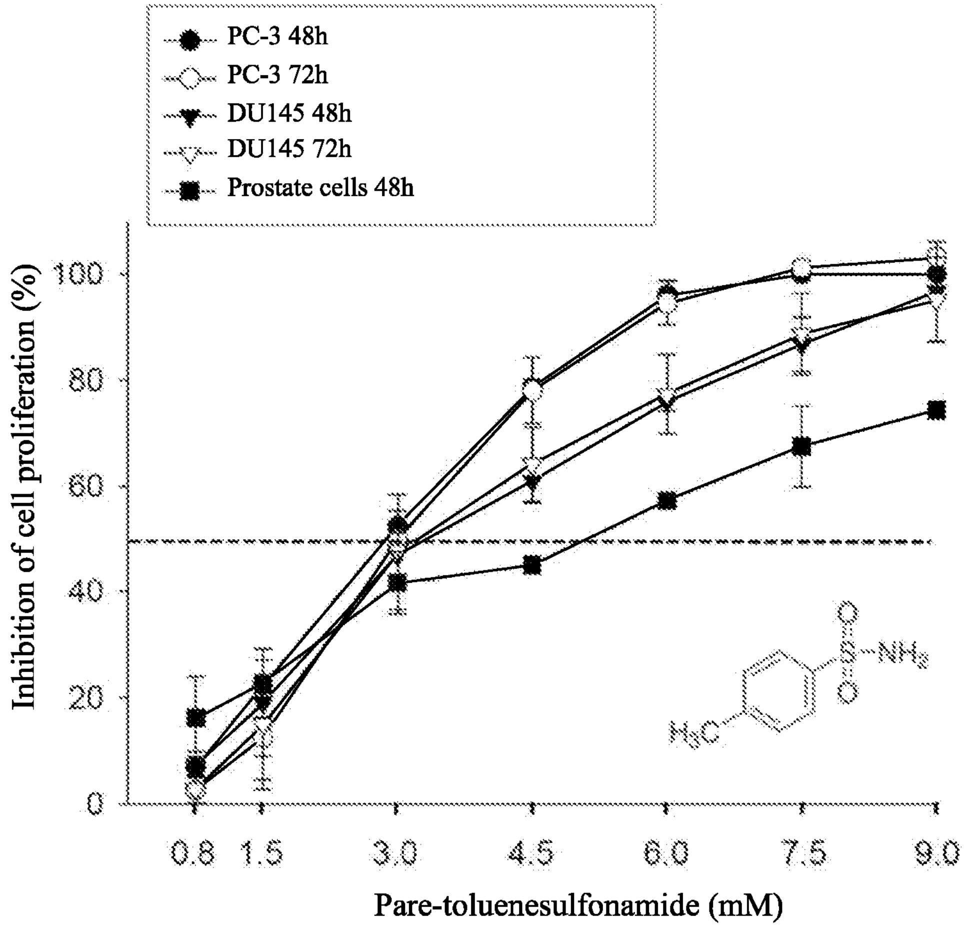
FIGS. 1A to 1D show the effect of p-TSA on anti-proliferative effects of human castration-resistant prostate cancer cells and primary prostate cells. The cells were incubated in the absence or presence of p-TSA for the indicated time. After treatment, the cells were fixed and stained for SRB assay (FIG. 1A) and colony formation assay (FIG. 1B). PC-3 cells and DU-145 cells were incubated with or without p-TSA. After treatment, the cells were harvested for flow cytometric analysis of CFSE staining (FIGS. 1C and 1D). The proliferation index and the cell populations of parent or different generations were calculated by Modfit LT Version 3.2 and WinList Version 5.0 software. Quantitative data are expressed as mean±SEM of three to four independent experiments. *** $P<0.001$ compared with the control.

The following examples are used to exemplify the present disclosure. A person of ordinary skill in the art can conceive the other advantages of the present disclosure, based on the specification of the present disclosure. The present disclosure can also be implemented or applied as described in different examples. It is possible to modify and/or alter the above examples for carrying out this disclosure without contravening its spirit and scope, for different aspects and applications.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The present disclosure provides a pharmaceutical composition comprising a benzenesulfonamide derivative, and a pharmaceutically acceptable excipient thereof.

In one embodiment of the present disclosure, the benzenesulfonamide derivative is represented by formula (I):

(I)

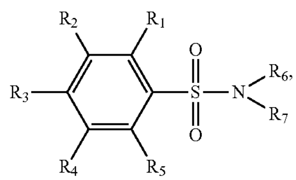

or a pharmaceutically acceptable salt thereof, wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring.

In an embodiment of the present disclosure, the alkyl, alkoxy, cycloalkyl, cycloheteroalkyl and the ring in $R_1$ to $R_7$ are independently unsubstituted or substituted with one or more substituents. In another embodiment of the present disclosure, the substituent is selected from the group consisting of phenyl, halo, oxo, ether, hydroxyl, carboxyl, amino, sulfo and sulfonamide group.

In one embodiment of the present disclosure, the benzenesulfonamide derivative may include, but is not limited to, para-toluenesulfonamide, ortho-toluenesulfonamide, meta-toluenesulfonamide, N-ethyl-para-toluene sulfonamide, N-ethyl-ortho-toluene sulfonamide, N-cyclohexyl-para-toluene sulfonamide,

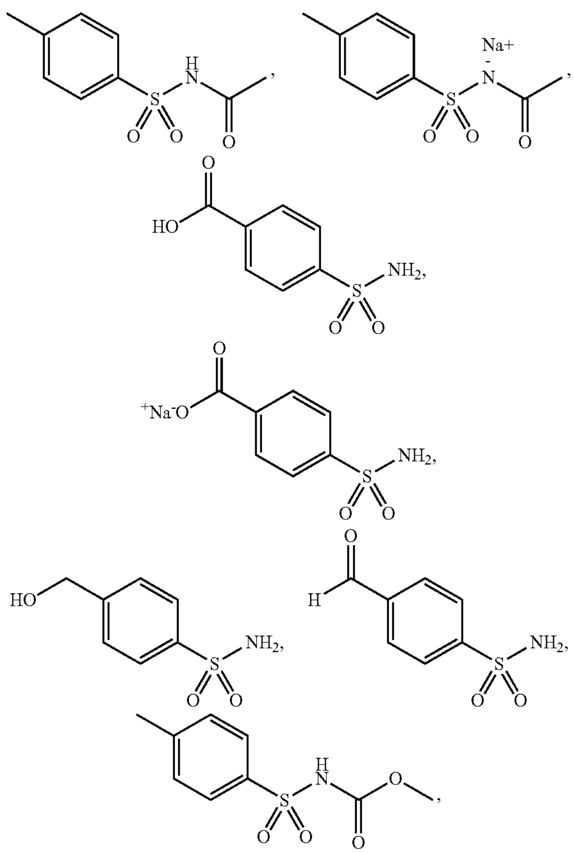

-continued

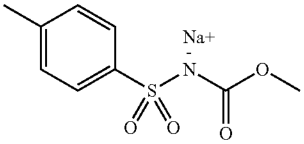

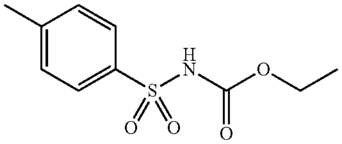

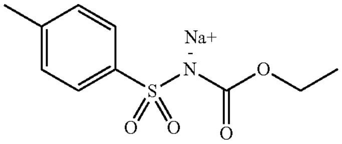

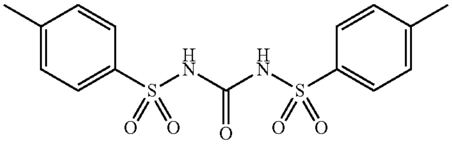

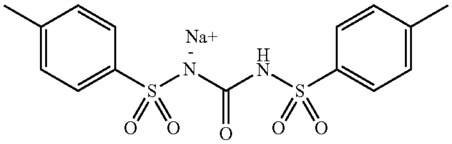

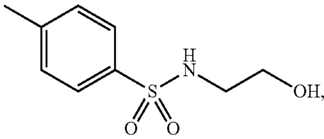

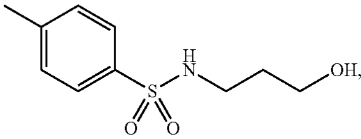

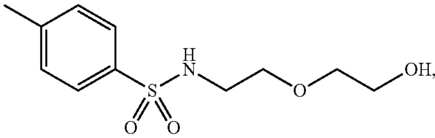

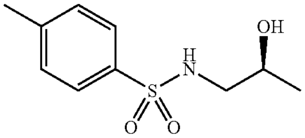

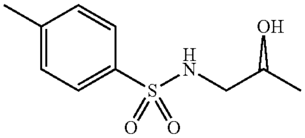

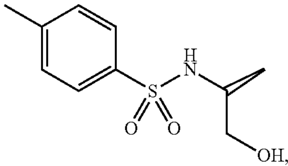

-continued
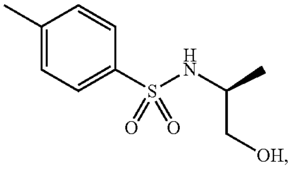
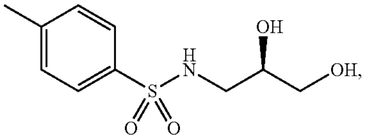
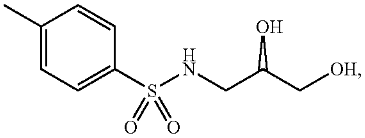
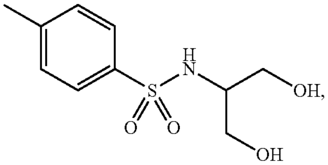
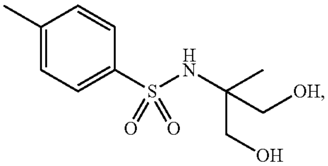
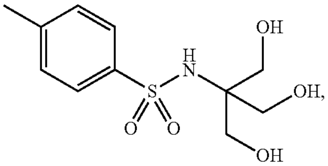
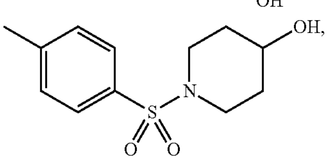
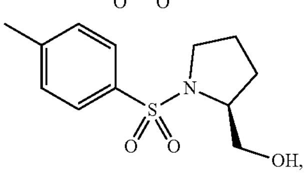
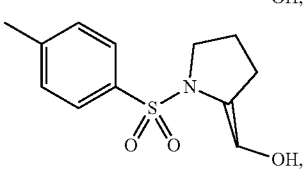
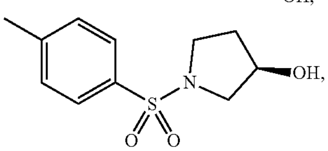
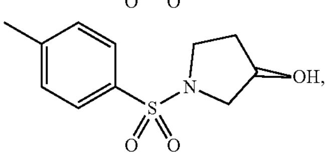
-continued
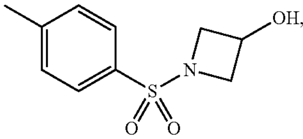
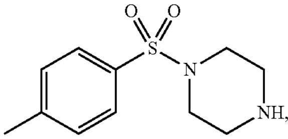
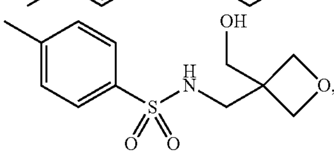
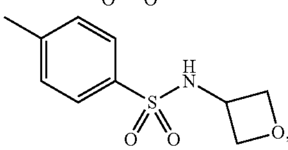
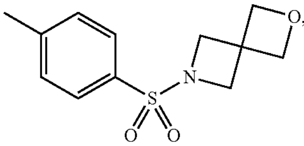
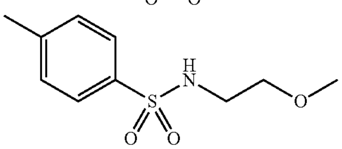
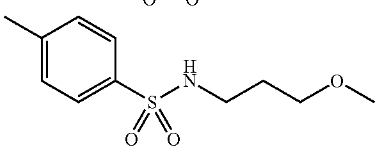
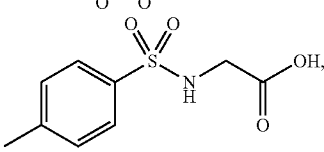
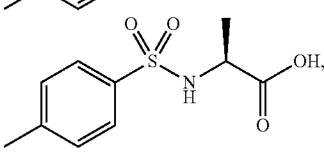
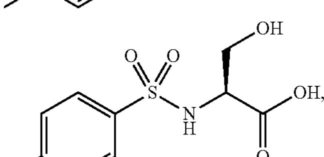
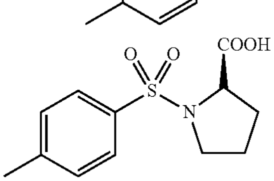
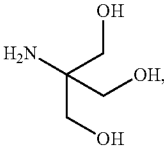
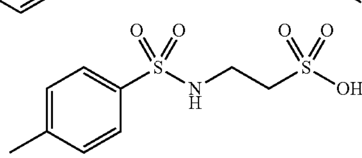

-continued

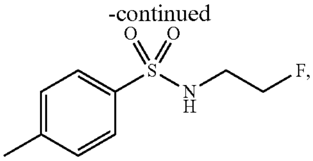

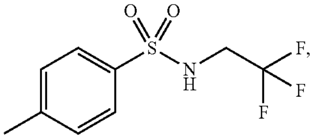

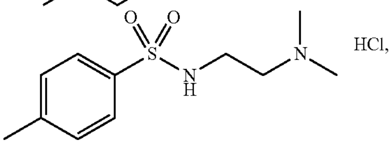

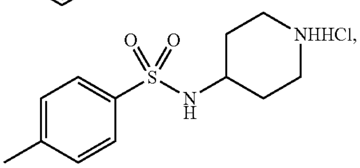

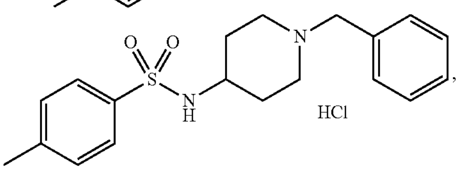

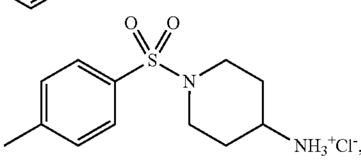

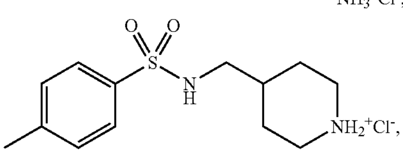

and

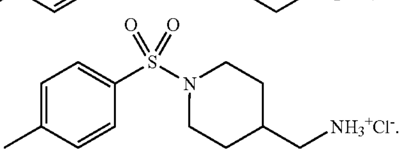

In one embodiment of the present disclosure, the benzenesulfonamide derivative is para-toluenesulfonamide (p-TSA).

In one embodiment of the present disclosure, the pharmaceutically acceptable excipient may be a filler, a binder, a preservative, a disintegrating agent, a lubricant, a suspending agent, a wetting agent, a solvent, a surfactant, an acid, a flavoring agent, polyethylene glycol (PEG), alkylene glycol, sebacic acid, dimethyl sulfoxide, alcohol or a combination thereof.

In one embodiment of the present disclosure, the benzenesulfonamide derivative is present in an amount ranging from about 5% to about 60% by weight.

In one embodiment of the present disclosure, the pharmaceutical composition is in a form suitable for parenteral administration, injection, continuous infusion, sublingual administration, subcutaneous administration or oral administration.

In one embodiment of the present disclosure, the form of the pharmaceutical composition comprises, but is not limited to, an injection formulation, dry powder, a tablet, oral liquid, a wafer, a film, a lozenge, a capsule, granule, or a pill.

The present disclosure also provides a method for modulating lipid raft integrity of a cell, comprising administering the pharmaceutical composition to a subject in need of treatment for modulating lipid raft integrity.

In one embodiment of the present disclosure, the pharmaceutical composition disturbs or disrupts the lipid raft integrity. In one embodiment of the present disclosure, the pharmaceutical composition depletes cholesterol from the plasma membrane of the cell.

In one embodiment of the present disclosure, the method may be used to treat a disease susceptible to amelioration by the decreased level of the lipid raft integrity. In another embodiment of the present disclosure, the disease is a cancer.

The present disclosure also provides a method for preventing or treating cancer, comprising administering the pharmaceutical composition to a subject in need thereof.

In one embodiment of the present disclosure, the benzenesulfonamide derivative in the pharmaceutical composition is administered to the subject in a therapeutically effective amount of from about 20 mg to about 4000 mg per day.

In one embodiment of the present disclosure, the pharmaceutical composition is administered to the subject intratumorally, intravenously, subcutaneously, intradermally, orally, intrathecally, intraperitoneally, intranasally, intramuscularly, intrapleuraly, or through nebulization.

In one embodiment of the present disclosure, the benzenesulfonamide derivative is served as a lipid raft modulating agent for inhibiting tumor growth of the cancer. In another embodiment of the present disclosure, the level of lipid raft integrity is decreased in tumor cells of the cancer. In another embodiment of the present disclosure, the level of total or phosphorylated form of the raft-associated kinase is decreased in tumor cells of the cancer. In another embodiment of the present disclosure, the cancer is at least one selected from the group consisting of lung cancer (including, but not limited to, non-small cell lung cancer, pulmonary squamous cell carcinoma, small cell lung cancer, lung adenocarcinoma), breast cancer, liver cancer (including, but not limited to, hepatocellular carcinoma), prostate cancer, skin cancer, pancreas cancer (including, but not limited to, pancreatic adenocarcinoma), melanoma, kidney cancer (including, but not limited to, renal cell carcinoma), bladder cancer (including, but not limited to, urothelial carcinoma), seminoma, ovarian cancer, cervical cancer, colon cancer, esophageal cancer (including, but not limited to, esophageal squamous cell carcinoma), oral cancer (including, but not limited to, oral squamous cell carcinoma), tongue cancer (including, but not limited to, tongue squamous cell carcinoma), thyroid cancer, meningiomas, bile duct cancer, hypopharyngeal cancer (including, but not limited to, hypopharyngeal squamous cell carcinoma), nasopharyngeal cancer, gastric cancer, and vulvar cancer (including, but not limited to, vulvar squamous cell carcinoma).

In one embodiment of the present disclosure, the benzenesulfonamide derivative is served as a cholesterol-depleting agent for inhibiting tumor growth of the cancer. In another embodiment of the present disclosure, the level of the cholesterol is decreased in tumor cells of the cancer. In another embodiment of the present disclosure, the cancer is at least one selected from the group consisting of lung cancer, breast cancer, liver cancer, skin cancer, prostate cancer, myeloid leukemia and oral cancer.

In one embodiment of the present disclosure, the benzenesulfonamide derivative disrupts the lipid rafts/caveolae molecular platforms that spatially organize appropriate molecules to inhibit specific signaling pathways including, but not limited to, Akt inactivation.

In one embodiment of the present disclosure, the method further comprises administering at least one additional anti-cancer agent to the subject.

In one embodiment of the present disclosure, the method further comprises administering at least one additional anti-cancer therapy to the subject, wherein the anti-cancer therapy comprises, but is not limited to, whole body chemotherapy, radiotherapy, or thermal therapy.

The following are specific embodiments further demonstrating the efficacy of the current disclosure, but not to limit the scope of the current disclosure.

EXAMPLE

Castration-resistant prostate cancer (CRPC) cells can resist many cellular stresses to ensure survival. There is an unmet medical need to fight against the multiple adaptive mechanisms in cells to achieve optimal treatment in patients. By the following examples, the present disclosure was demonstrated that para-toluenesulfonamide (p-TSA) is a small molecule that inhibited cell proliferation of PC-3 and DU-145, two CRPC cell lines, through p21- and p27-independent G1 arrest of cell cycle in which cyclin D1 was down-regulated and Rb phosphorylation was inhibited. p-TSA also induced a significant loss of mitochondrial membrane potential that was attributed to up-regulation of both Bak and PUMA, two pro-apoptotic Bcl-2 family members, leading to apoptosis. p-TSA inhibited the phosphorylation of m-TOR, 4E-BP1 and p70S6K in both cell lines. Overexpression of constitutively active Akt rescued the inhibition of mTOR/p70S6K signaling in PC-3 cells, indicating an Akt-dependent pathway. In contrast, the Akt-independent effect was observed in DU-145 cells. Lipid rafts serve as functional platforms for multiple cellular signaling and trafficking processes. Both cell lines expressed raft-associated Akt, mTOR and p70S6K. p-TSA induced decreases of expressions in both raft-associated total and phosphorylated forms of these kinases. p-TSA-induced inhibitory effects were rescued by supplement of cholesterol, an essential constituent in lipid raft, indicating a key role of cholesterol contents. Moreover, the tumor xenograft model showed that p-TSA inhibited tumor growth with a T/C (treatment/control) of 0.44 and a 56% inhibition of growth rate indicating the in vivo efficacy. In conclusion, the data suggest that p-TSA is an effective anti-tumor agent with in vitro and in vivo efficacies through inhibition of both Akt-dependent and -independent mTOR/p70S6K pathways. Moreover, disturbance of lipid raft and cholesterol contents may explain the p-TSA-mediated anti-tumor process.

The sources of materials used in the examples of the present disclosure are shown as follows. Human prostate adenocarcinoma cell lines, PC-3 and DU-145, were obtained from American Type Culture Collection (Rockville, MD, United States). RPMI 1640 medium, fetal bovine serum (FBS), penicillin and streptomycin were purchased from GIBCO/BRL Life Technologies (Grand Island, NY, United States). Antibodies of PARP-1, Bcl-2, Bak, Mcl-1, p53 upregulated modulator of apoptosis (PUMA), α-tubulin, cyclin E, cyclin A, cyclin B, cyclin-dependent kinase (Cdk) 4, Cdk2, Cdk1, GAPDH, p27, and caveolin-1 were obtained from Santa Cruz Biotechnology, Inc. (Santa Cruz, CA, United States). Antibodies of Rb, p-Rb$^{Ser807/811}$, p21, Akt, p-Akt$^{Thr308}$, p-Akt$^{Ser473}$, Bid, cyclin D1, mTOR, p-mTOR$^{Ser2448}$, 4E-BP1, p-4E-BP1$^{Thr37/46}$, p-p70S6K$^{Thr389}$ and p-IκB-α$^{Ser32}$ were from Cell Signaling Technologies (Boston, MA, United States). P70S6K was from Abcam (Cambridge, United Kingdom). Caspase-3 was from Imgenex, Corp. (San Diego, CA, United States). Carboxyfluorescein succinimidyl ester (CFSE) was from Molecular Probes Inc. (Eugene, OR, United States). Anti-mouse and anti-rabbit IgGs were from Jackson ImmunoResearch Laboratories, Inc. (West Grove, PA, United States). para-toluenesulfonamide (p-TSA), sulforhodamine B (SRB), leupeptin, NaF, $NaVO_4$, dithiothreitol, phenylmethylsulfonylfluoride (PMSF), trichloroacetic acid (TCA), mitoxantrone, water-soluble cholesterol, propidium iodide (PI) and all other chemical compounds were purchased from Sigma-Aldrich (St. Louis, MO, United States).

Example 1: Examination of the Effect of p-Toluenesulfonamide (p-TSA) on Inhibiting Cell Proliferation in Castration-Resistant Prostate Cancer (CRPC) Cells Two castration-resistant prostate cancer (CRPC) cell lines of PC-3 and DU-145 were cultured in RPMI 1640 medium with 5% FBS (v/v), penicillin (100 units/ml) and streptomycin (100 μg/ml). Cultures were maintained in a 37° C. incubator with 5% $CO_2$, and adherent cultures were passaged using 0.05% trypsin-EDTA when they reached about 80% confluence. Prostate cells were from human tissue samples which were obtained following informed consent of the donors and after full review by the Ethics Review Committee at National Taiwan University Hospital. The prostate specimens were from males by transurethral resection of the prostate. All patients with prostatism histories were diagnosed to have benign prostate hyperplasia by rectal digital examination, transrectal sonography of prostate and urodynamic studies. Isolation of human prostatic cells from prostatic tissue explants was described in the previous study [22]. The prostate cells were with less amount lipid rafts compared to prostate cancer cells.

SRB assay, colonogenic assay, and carboxyfluorescein succinimidyl ester (CFSE) staining were used for anti-proliferative determination. SRB assay is an accurate and reproducible assay based upon quantitative SRB staining of cellular proteins, and the process for SRB assay was performed as follows. Each individual PC-3 and DU-145 cells were seeded in 96-well plates in medium with 10% FBS. After 24 h, PC-3 and DU-145 cells were fixed with 10% TCA to represent cell population at the time of p-TSA addition. After additional incubation of DMSO or p-TSA for 48 or 72 h, the cells were fixed with 10% TCA, and then SRB at 0.4% (w/v) in 1% acetic acid was added to stain PC-3 and DU-145 cells. Unbound SRB was washed out by 1% acetic acid, and SRB bound cells were solubilized with 10 mM Tris base. The absorbance of SRB was measured at a wavelength of 515 nm at the time of p-TSA addition (hereinafter referred to as time zero, TZ), and after additional incubation of DMSO (hereinafter referred to as control growth, CTL) or p-TSA (hereinafter referred to as Tx). The percentage of cell growth inhibition was calculated by the formula of $[1-(Tx-TZ)/(CTL-TZ)]\times100\%$. 50% inhibition of cell growth ($IC_{50}$) is determined at the p-TSA concentration which results in 50% reduction of total protein increase in the control cells during p-TSA incubation.

To assay the anchorage-dependent clonogenic effect, each individual PC-3 and DU-145 cells (150 cells/well) were seeded in a 6-well plate. After a 10-day treatment with p-TSA, the cell colonies were rinsed with phosphate-buffered saline (PBS), stained with 0.4% (w/v) crystal violet dissolved in 20% methanol, and lysed by 50 mM sodium citrate dissolved in 50% ethanol. The absorbance was read at a wavelength of 595 nm.

Figure 1B:
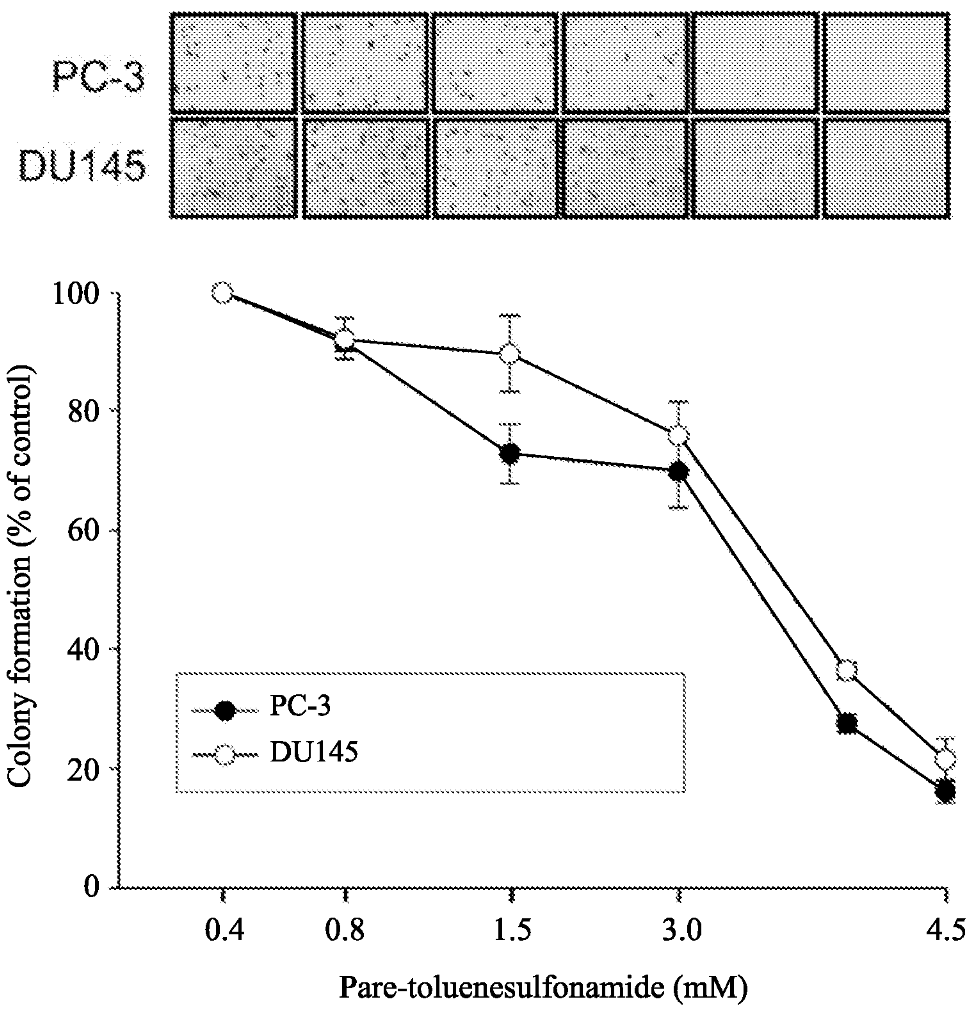

As the results shown in FIG. 1A, p-TSA showed a concentration-dependent inhibition of both PC-3 and DU-145 cell lines with $IC_{50}$ values around 3 mM. In addition, the data also showed that p-TSA displayed a lower anti-proliferative activity in normal prostate cells. Moreover, as the results shown in FIG. 1B, the clonogenic assay demonstrated that p-TSA displayed a long-term anti-proliferative effect (10 days) in both PC-3 and DU-145 cells.

The anti-proliferative effect was further examined by CFSE staining. CFSE is a fluorescent cell staining dye for cell-tracking, and it was conjugated to intracellular proteins and was evenly inherited by divided cells after cell proliferation. Consequently, the fluorescence-staining was distributed to later generations of cells with the passage of time. The process for CFSE staining was performed as follows. CFSE was dissolved in DMSO to constitute a storage solution of 10 mM and was kept at −20° C. until use. The PC-3 and DU-145 cells were adjusted to a density of $10^6$ cells/ml and were treated with CFSE at a final concentration of 10 μM in tubes. After incubation at 37° C. for 10 min, labeling was blocked by the addition of RPMI medium with 10% FBS. The tubes were placed on ice for 5 min and then washed. After centrifugation of the tubes, the cells were seeded in RPMI medium with 10% FCS in the absence or presence of p-TSA for 48 h at 37° C. under 5% $CO_2$/95% air condition. The fluorescence intensity was determined by flow cytometric analysis. The cell proliferation was assessed by monitoring the decrease in label intensity in daughter cells. The proliferation index and the cell populations of parent or different generations were calculated by using Modfit LT Version 3.2 and WinList Version 5.0 software.

Flow cytometric analysis was performed as follows. Cells were harvested by trypsinization, fixed with 70% (v/v) alcohol at 4° C. for 30 min and washed with PBS. After centrifugation, the cells were incubated in phosphate-citric acid buffer (0.2 mol/l $NaHPO_4$, 0.1 mol/l citric acid, pH 7.8) for 30 min at room temperature. The cells were then centrifuged and resuspended with 0.5 ml propidium iodide (PI) solution containing Triton X-100 (0.1% v/v), RNase (100 μg/ml) and PI (80 μg/ml). DNA content was analyzed with the FACScan and CellQuest software (Becton Dickinson, Mountain View, CA, United States).

Figure 1C:
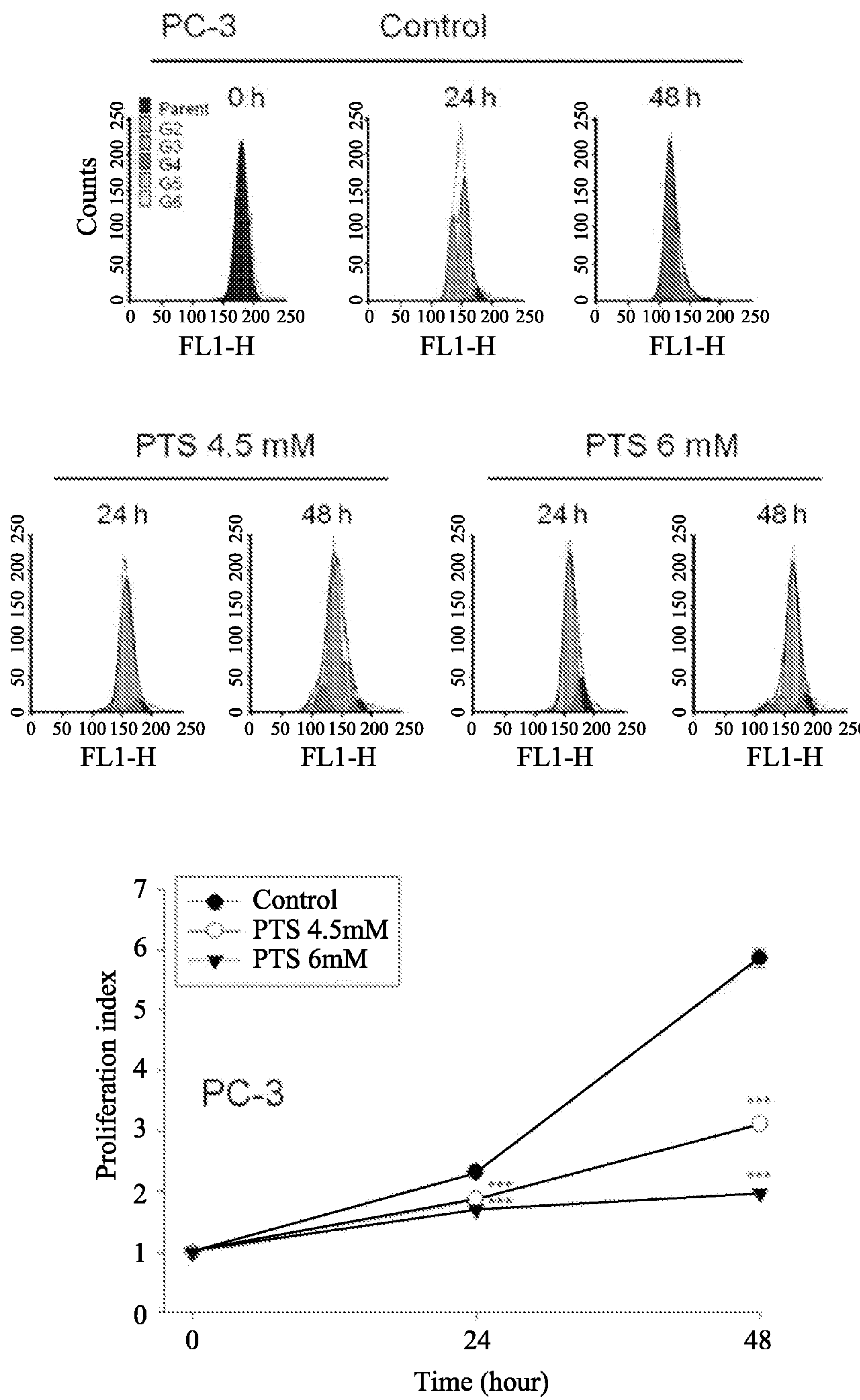
Figure 1D:
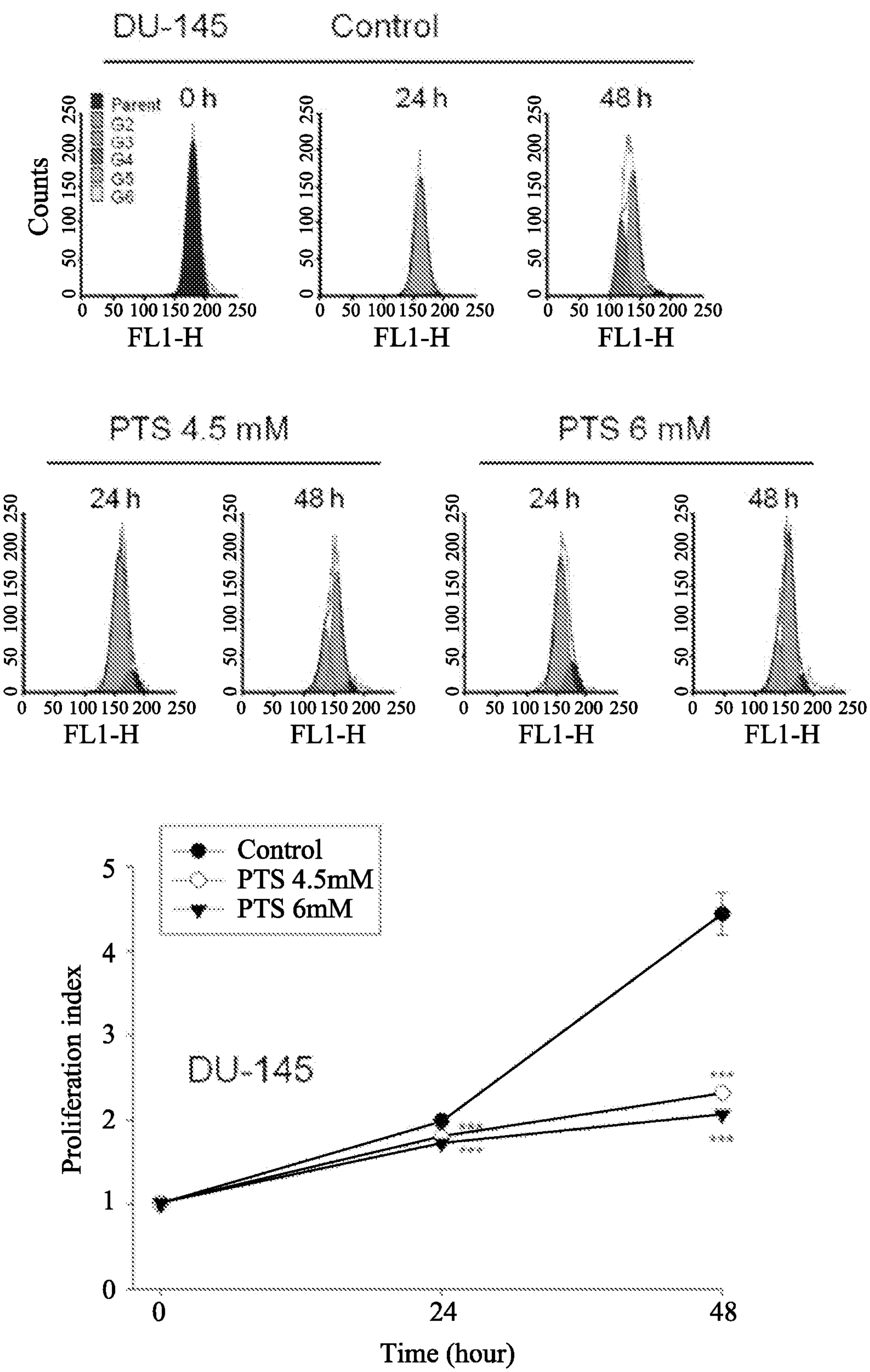

As shown in FIGS. 1C and 1D, p-TSA significantly inhibited cell proliferation, inducing an increase of cell population in earlier generations. The proliferation index in both PC-3 and DU-145 cells based on CFSE staining assay showed a concentration-dependent inhibition to p-TSA action. Because p-TSA is a simple small molecule with a molecular weight of 171 Dalton, it is reasonable that p-TSA is effective with concentrations in millimolar range. Several other compounds and drugs also have been reported to display activities at millimolar concentrations, such as N-acetylcysteine and trolox in scavenging reactive oxygen species (ROS), and aspirin and epigallocatechin-3-gallate in inducing cell-cycle arrest and apoptotic cell death [23, 24].

From the above, it could be seen that p-TSA inhibited proliferation of CRPC cells.

Figure 2A:
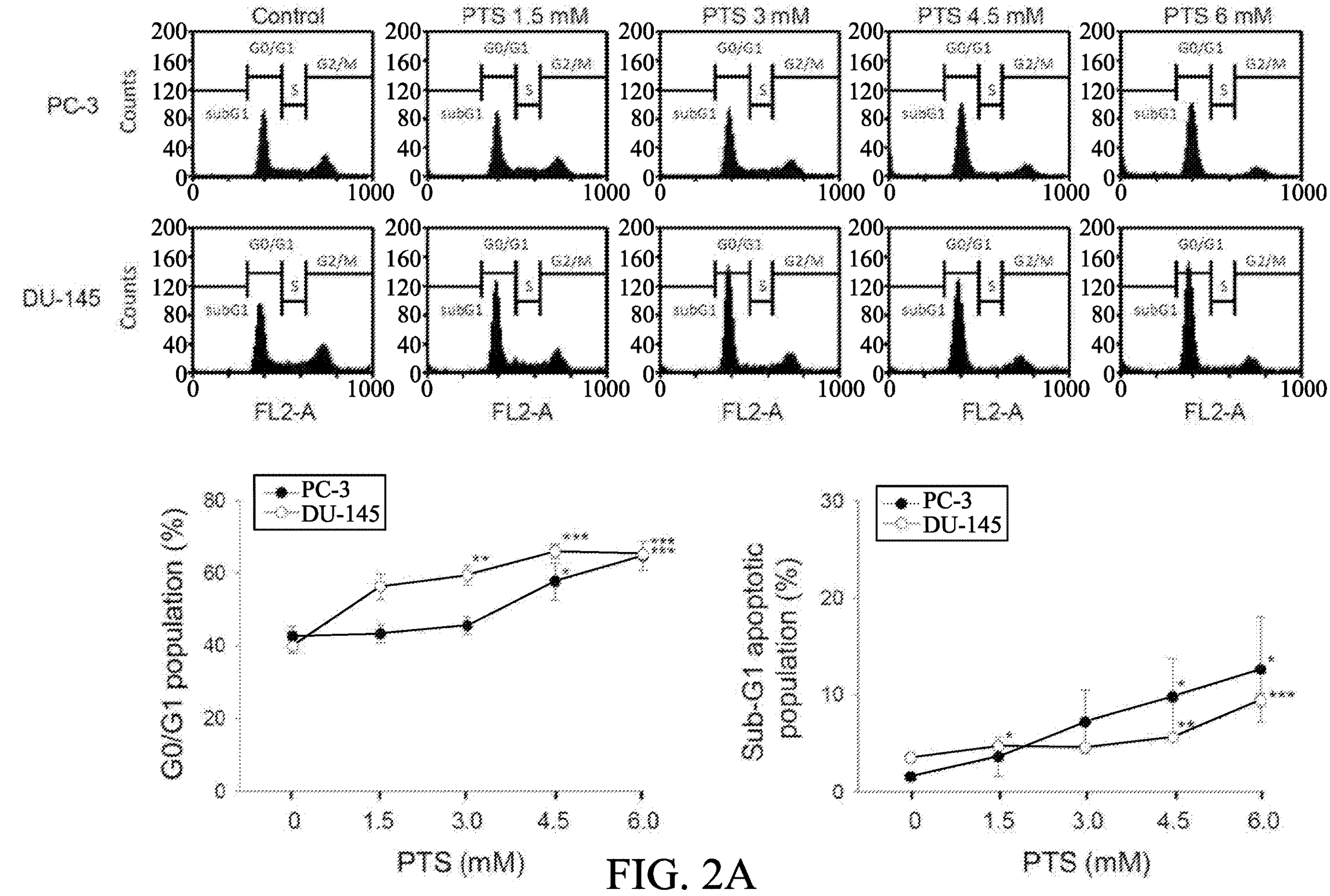
FIGS. 2A to 2D show the effect of p-TSA on cell cycle arrest and mitochondrial dysfunction. PC-3 and DU-145 cells were incubated in the absence or presence of p-TSA for 24 h. The cells were harvested for propidium iodide staining to analyze the distribution of cell populations in cell cycle phases (FIG. 2A), or for JC-1 staining to detect mitochondrial membrane potential using FACScan flow cytometric analysis (FIG. 2B). The green fluorescence was shown for the quantification of mitochondrial membrane potential (FIG. 2B). The cells were harvested and lysed for the detection of protein expressions of several Bcl-2 family members by Western blot analysis (FIGS. 2C and 2D). Data are expressed as mean±SEM of three to four determinations. * $P<0.05$,  $P<0.01$ and * $P<0.001$ compared with the control.

Example 2: Examination of the Effect of p-TSA on Cell Cycle Progression and Mitochondrial Stress As shown in FIG. 2A, p-TSA induced accumulation of both PC-3 cells and DU-145 cells in G1 phase of the cell cycle and accelerated cell apoptosis. Cell cycle checkpoints are critical mechanisms to ensure proper cell division. The G1 checkpoint is the major one at which the cell becomes committed to entering cell cycle. When DNA damage or certain cellular stresses occur, G1 arrest takes place until the damage is fixed. If not properly repaired, apoptosis would be triggered through the inhibition of pro-survival components or the activation of apoptotic pathways in which mitochondria are the most sensitive organelles to orchestrate these signals.

Figure 2B:
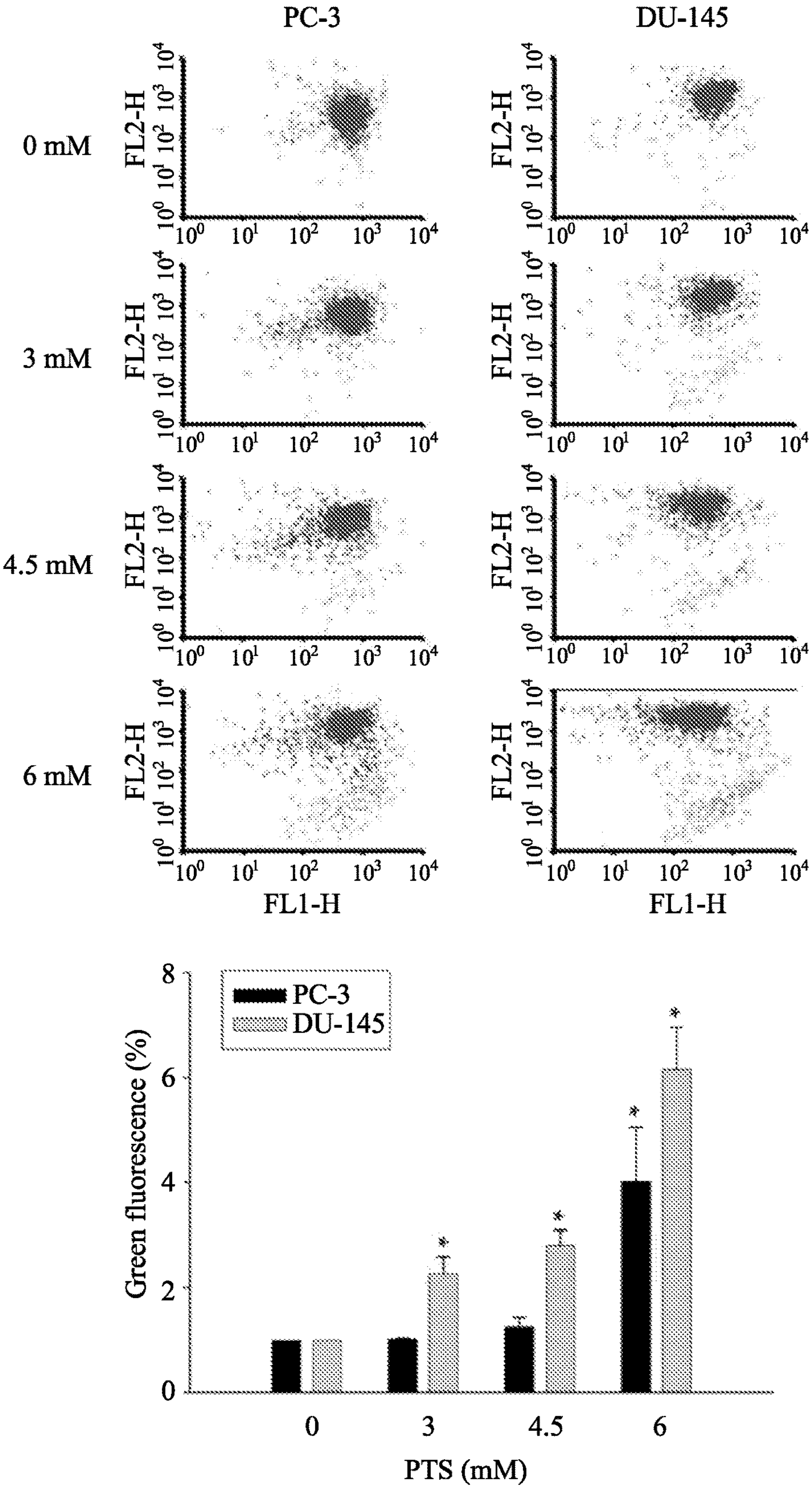

Mitochondria generate the majority of ATP to synthesize bioactive components such as proteins, lipids and nucleotides for cell growth and proliferation. The stress onto mitochondria and interference with ATP production have shown to induce cell cycle arrest [25]. Measurement of mitochondrial membrane potential (ΔΨm) was performed as follows. JC-1, a mitochondrial dye staining mitochondria in living cells in a membrane potential-dependent fashion, was used to determine the mitochondrial membrane potential (ΔΨm). PC-3 and DU145 cells were treated with or without p-TSA. Thirty minutes before the termination of incubation, the cells were incubated with JC-1 (final concentration of 5 μM) at 37° C. for 30 min. The cells were finally harvested, and the accumulation of JC-1 was determined using flow cytometric analysis. As shown in FIG. 2B, p-TSA resulted in a concentration-dependent decrease of mitochondrial membrane potential, indicating that mitochondrial stress led to caspase-dependent apoptosis because Z-VAD-FMK, a pan-caspase inhibitor, profoundly inhibited PTS-induced apoptosis using both flow cytometric analysis of PI staining and nucleosomal DNA fragmentation assay (FIG. 2E and FIG. 2F). An increase in the permeability of the outer mitochondrial membrane that leads to the release of apoptogenic factors is the key to cell apoptosis. Mitochondrial membrane permeability is directly controlled by Bcl-2 family of proteins [26].

Figure 2C:
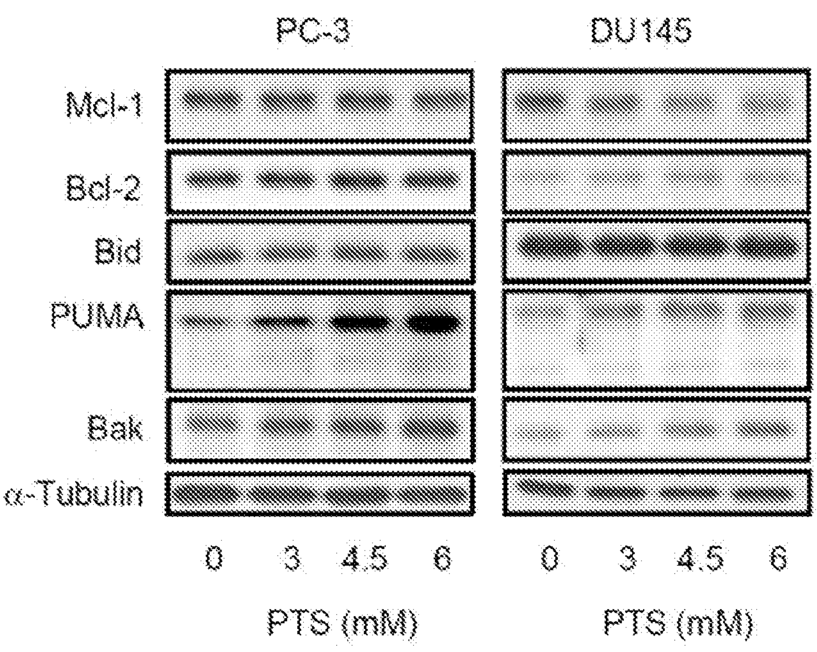
Figure 2D:
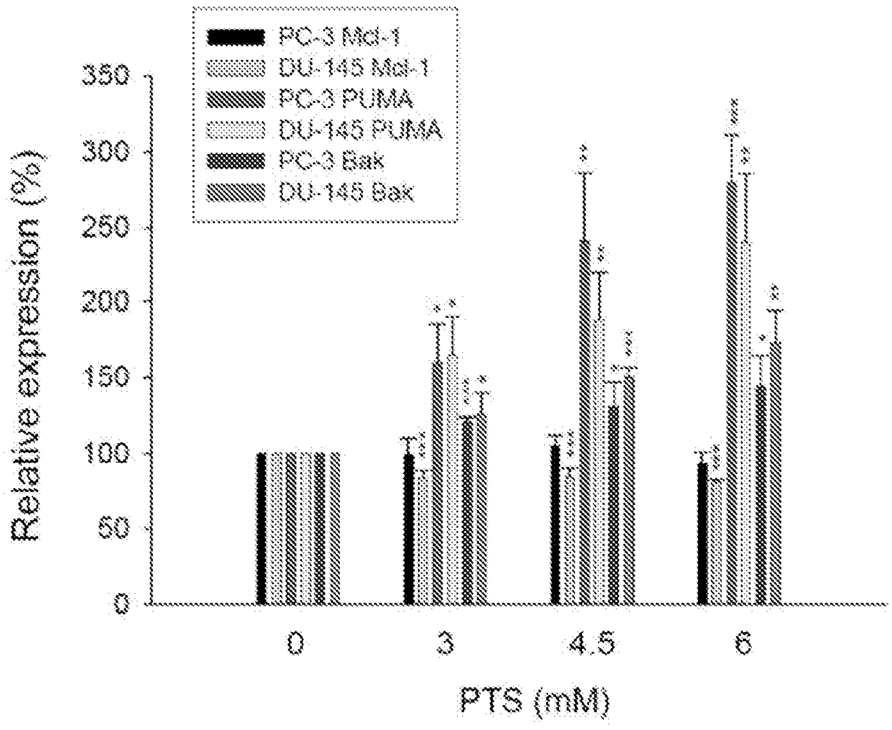
Figure 2E:
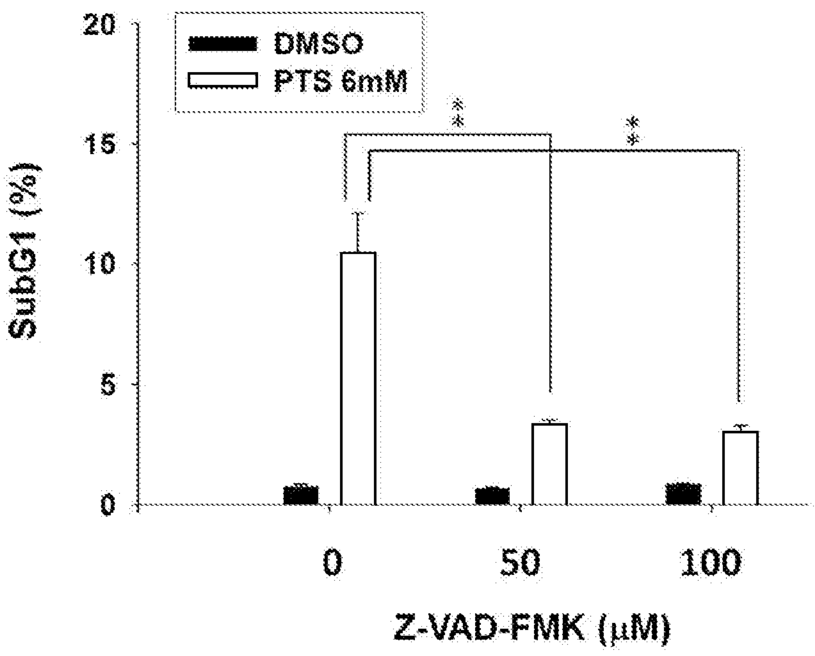
FIGS. 2E and 2F show the effect of Z-VAD-FMK on PTS-induced apoptosis in PC-3 cells. The cells were incubated in the absence or presence of the indicated agents for 24 hours. The cells were harvested for flow cytometric analysis of PI staining (FIG. 2E) of nucleosomal DNA fragmentation assay (FIG. 2F). Quantitative data are expressed as mean±SD of three independent experiments.  $P<0.01$ and * $P<0.001$ compared with the control.
Figure 2F:
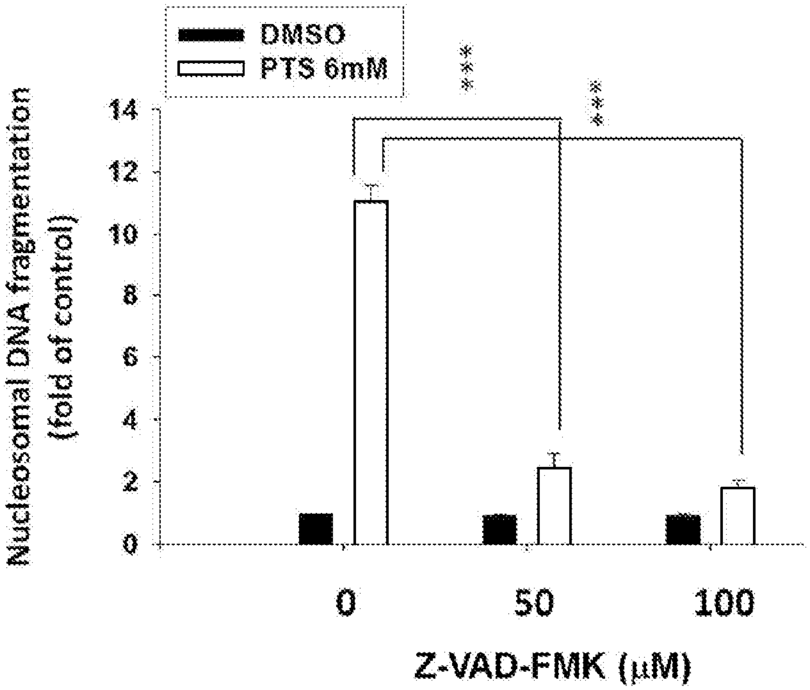

The data shown in FIGS. 2C and 2D demonstrated that p-TSA induced an increase in expressions of PUMA and Bak, two pro-apoptotic Bcl-2 family members in both PC-3 and DU-145 cells. In addition, protein expression assay of each Mcl-1, Bcl-2, Bid, PUMA and Bak was performed by western blotting with methods described as follows. After treatment of PC-3 and DU145 cells with p-TSA, the cells were harvested with trypsinization, centrifuged and lysed in 0.1 ml of lysis buffer containing 10 mM Tris-HCl (pH 7.4), 150 mM NaCl, 1 mM EGTA, 1% Triton X-100, 1 mM PMSF, 10 μg/ml leupeptin, 10 μg/ml aprotinin, 50 mM NaF and 100 μM sodium orthovanadate. Total protein was quantified, mixed with the sample buffer and boiled at 90° C. for 5 min. Equal amount of protein (30 μg) was separated by electrophoresis in 8% or 12% SDS-PAGE, transferred to PVDF membranes and detected with specific antibodies (1:1000 dilution) for each of Mcl-1, Bcl-2, Bid, PUMA and Bak proteins. The immunoreactive proteins after incubation with appropriately labeled secondary antibody (1:3000 dilution) were detected with an enhanced chemiluminescence detection kit (Amersham, Buckinghamshire, United Kingdom). Further, it was observed from FIG. 2D that p-TSA significantly decreased the protein expression of Mcl-1, an anti-apoptotic Bcl-2 family member, in DU-145 cells. These effects were correlated with the mitochondrial stress.

In G1 phase of the cell cycle, cyclin D1/Cdk4 complex is responsible for progression to S phase by the phosphorylation of the Rb protein. Cyclin D1/Cdk4 complex is able to reduce the activity of Cdk inhibitors (CDKIs) such as p21 and p27, triggering subsequent activation of cyclin E/Cdk2 complex which activates a number of proteins related to DNA synthesis [27].

The DNA fragmentation was determined for cell death determination by use of the Cell Death Detection ELISAplus kit (Roche, Mannheim, Germany) The assay was based on the quantitative in vitro determination of cytoplasmic histone-associated DNA fragments (mono- and oligonucleosomes) after induced cell death. After the treatment with the compound, the cells were lysed and centrifuged, and the supernatant was used for the detection of nucleosomal DNA according to the manufacturer's protocol.

Figure 3A:
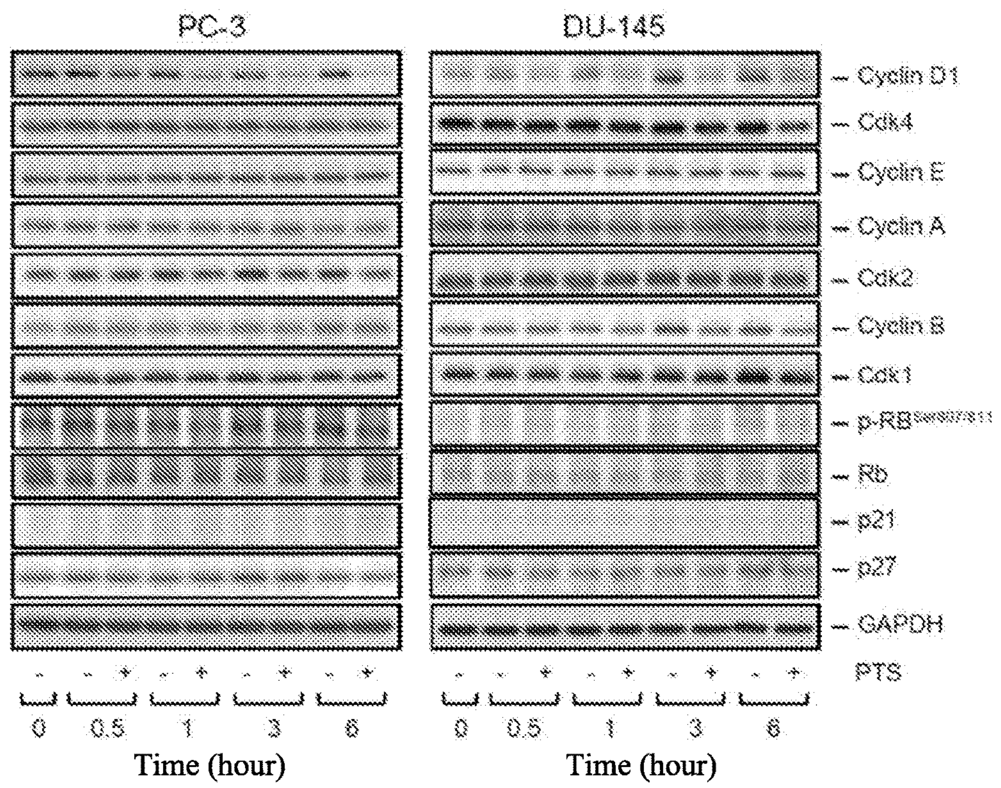
FIGS. 3A to 3C show the effect of p-TSA on the expression of cell cycle regulators and kinases. The cells were incubated in the absence or presence of 6 mM p-TSA for the indicated time. After treatment, the cells were harvested and lysed for the detection of protein expressions of cell cycle regulators (FIG. 3A), and Akt/mTOR/p70S6K pathway signals (FIG. 3B) by Western blot analysis. The expression was quantified using Image Lab Software 6.0 (BIO-RAD) (FIG. 3C). Data are expressed as mean±SEM of three determinations. * $P<0.05$,  $P<0.01$ and * $P<0.001$ compared with the control.

As shown in FIG. 3A, it demonstrated that p-TSA induced a decrease of both cyclin D1 protein expression and Rb phosphorylation in PC-3 cells, but only a decrease of cyclin D1 expression in Rb-mutant DU-145 cells. Also, neither p21 nor p27 expression was modified by p-TSA in both PC-3 and DU-145 cells. p-TSA-induced cyclin D1 down-regulation was correlated to G1 arrest of the cell cycle. However, the independency of both p21 and p27 in p-TSA-mediated G1 arrest might be explained by other factors and will be discussed below.

From the above, it could be seen that p-TSA provided the effect of inducing G1 arrest of the cell cycle and mitochondrial stress.

Figure 3B:
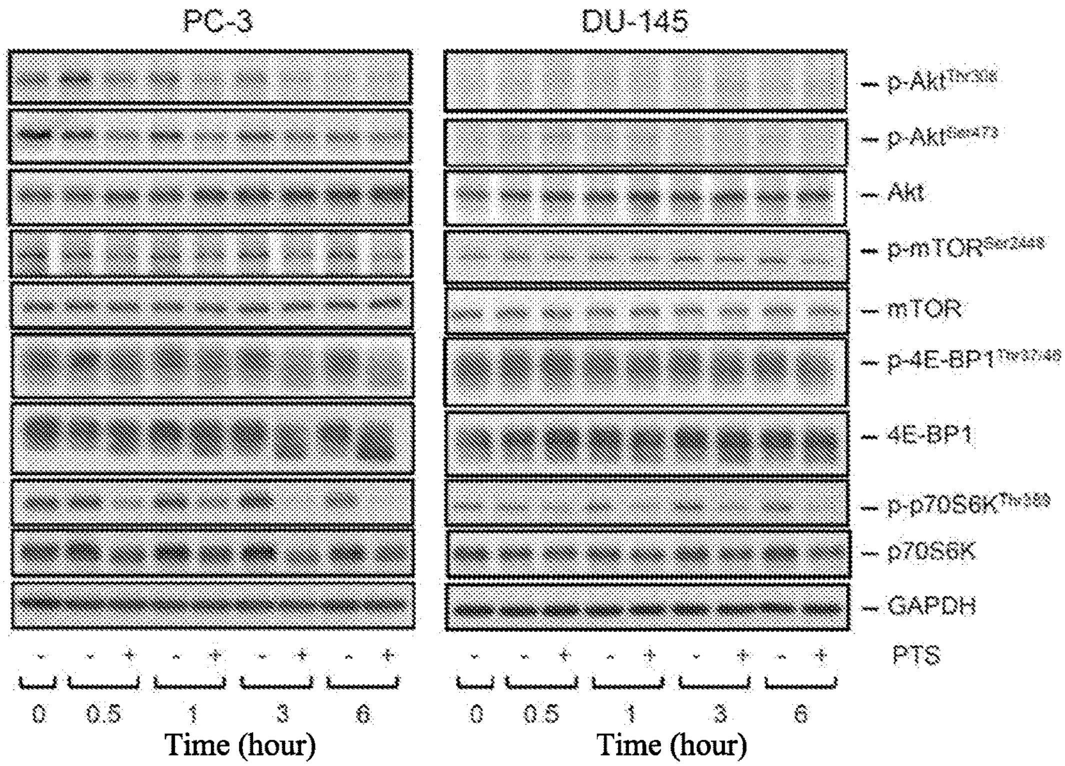
Figure 3C:
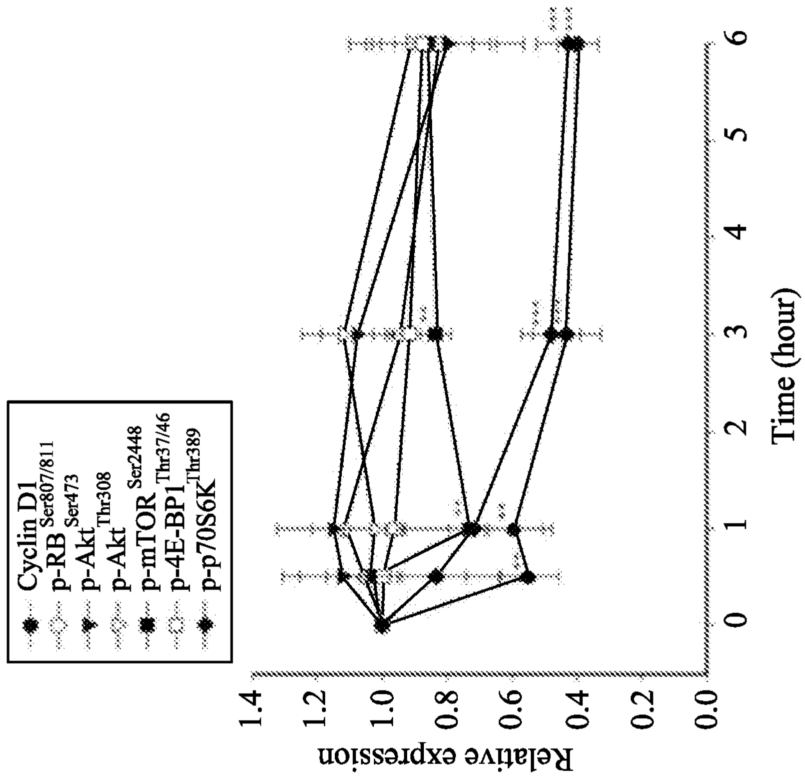
Figure 3C:
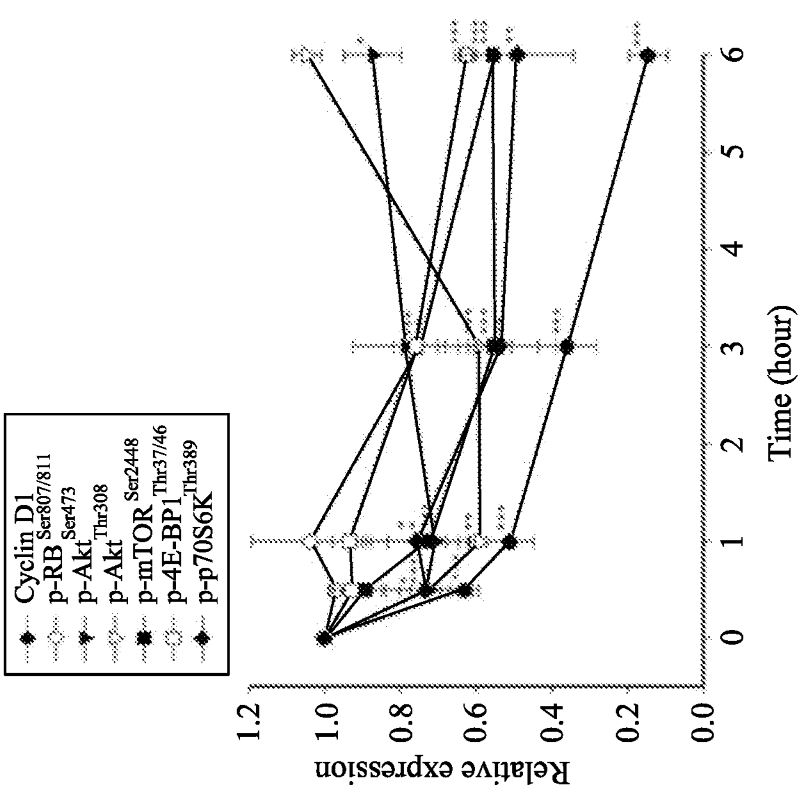

Example 3: Examination of the Effect of p-TSA on the Regulation of Akt/mTOR/p70S6K Pathway During G1 phase, cells grow in size and synthesize mRNA and proteins which are necessary to DNA synthesis. The serine/threonine kinases mTOR and p70S6K that regulate protein synthesis (mRNA translation) through affecting the phosphorylation or activities of several downstream translation factors are critical regulators in G1 phase [28-30]. Protein expression assay of each Akt, mTOR 4E-BP1 and p70S6K was performed by Western blotting. As shown in FIGS. 3B and 3C, it demonstrated that p-TSA induced an inhibitory effect on the phosphorylation of mTOR, 4E-BP1 (a repressor of mRNA translation) and p70S6K proteins in both PC-3 and DU-145 cells, which explained the inhibition of protein synthesis and anticancer effects on these cells. Moreover, p-TSA inhibited the phosphorylation of Akt, which is a critical player of signaling pathways of mTOR, 4E-BP1 and p70S6K, in PC-3 cells, indicating that the inhibition of Akt/mTOR/p70S6K axis activation could be responsible for p-TSA-mediated effects. In contrast, Akt phosphorylation was not modified by p-TSA in DU-145 cells, suggesting an Akt-independent mTOR/p70S6K signaling.

Figure 4A:
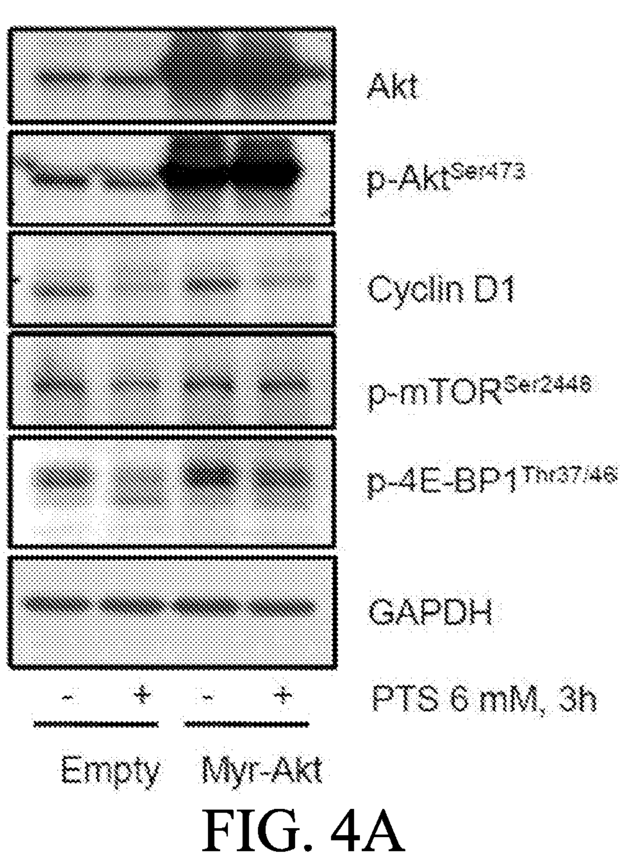
FIGS. 4A to 4D show the effect of Akt on PTS-induced alteration in several protein expressions. PC-3 cells were transfected with Myr-Akt plasmids. Then, the cells were incubated in the absence or presence of p-TSA for 3 h (FIG. 4A) or 24 h (FIG. 4B). The cells were harvested and lysed for the detection of the indicated protein by Western blot analysis. The expression was quantified using Image Lab Software 6.0 (BIO-RAD). The data are expressed as mean±SEM of three independent experiments.
Figure 4B:
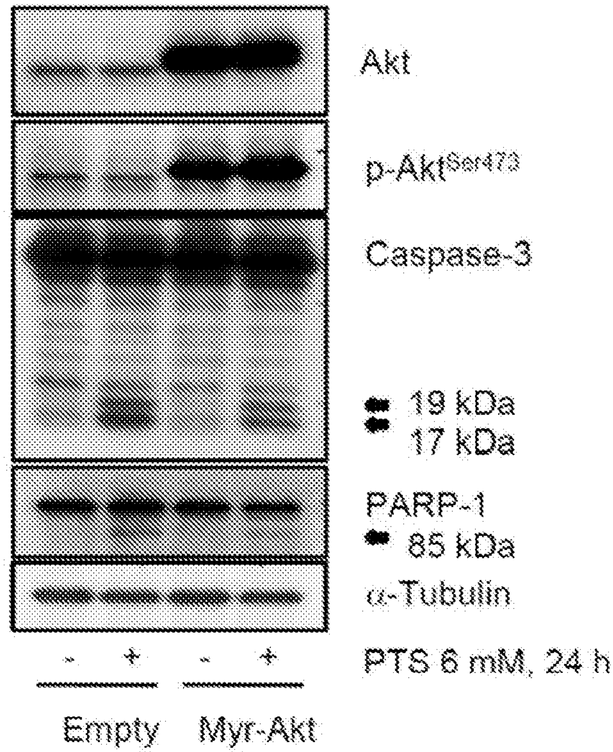
Figure 4C:
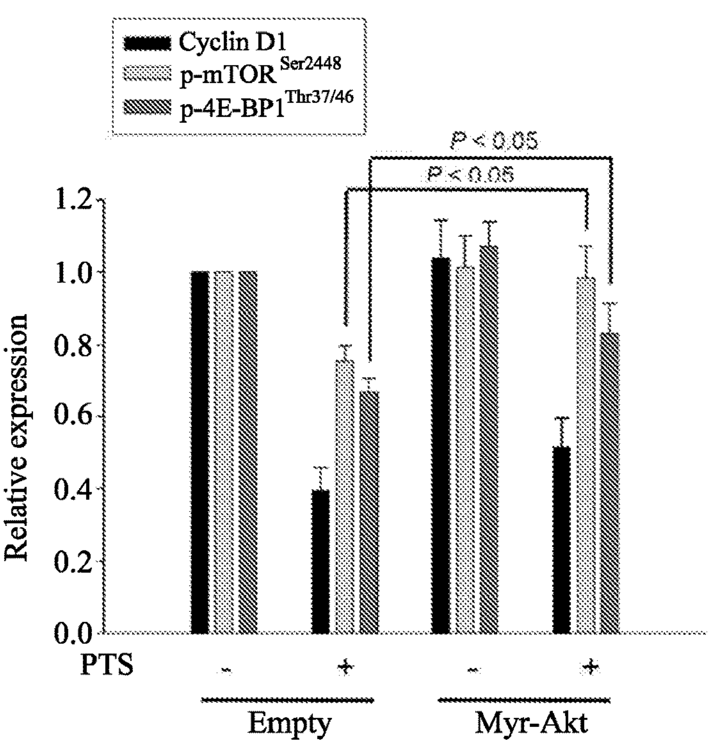
Figure 4D:
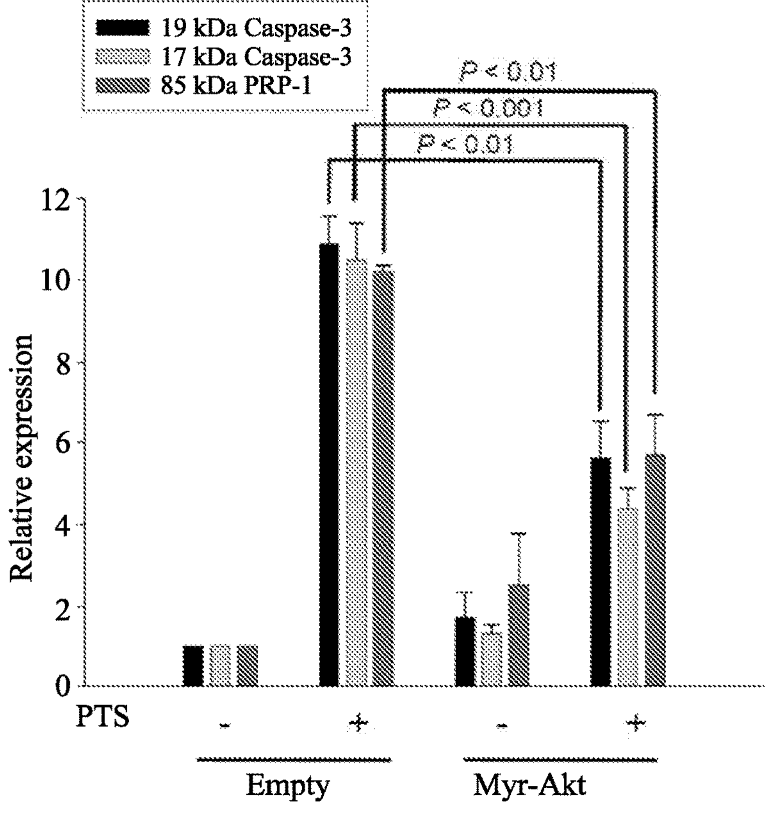
Figure 4E:
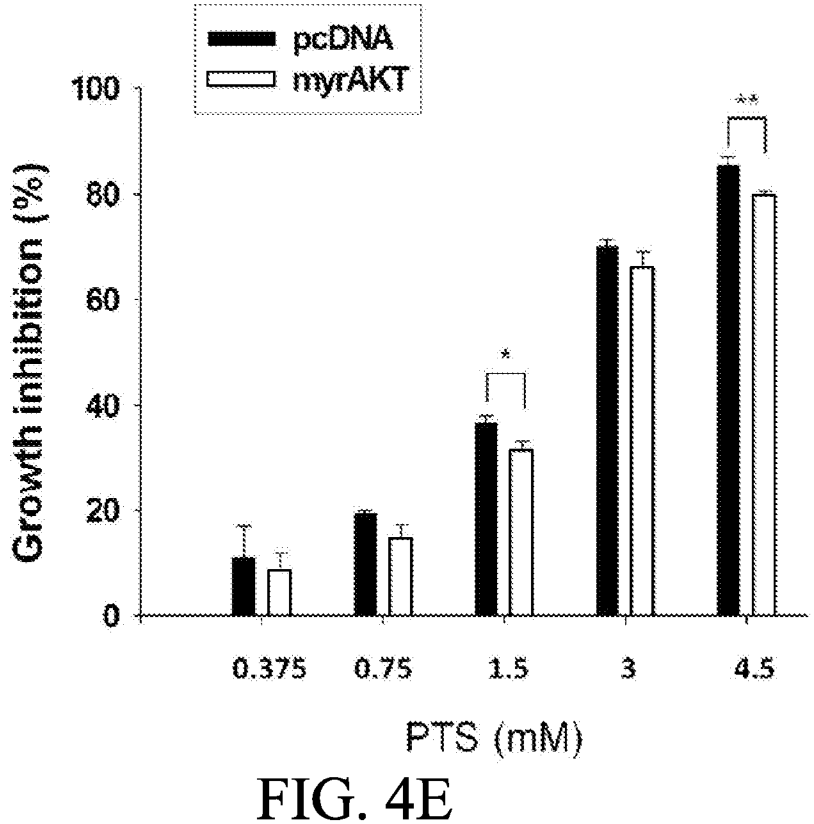
FIGS. 4E and 4F show anti-proliferative effects of PTS in PC-3 cells. The cells were incubated in the presence of the indicated condition. The cells were treated with or without PTS for 48 hours or 10 days for SRB (FIG. 4E) and colony formation assays (FIG. 4F), respectively. After treatment, cells were fixed and stained for the assays. Quantitative data are expressed as mean±SD of three independent experiments. * $P<0.05$ and ** $P<0.01$ compared with the respective control.
Figure 4F:
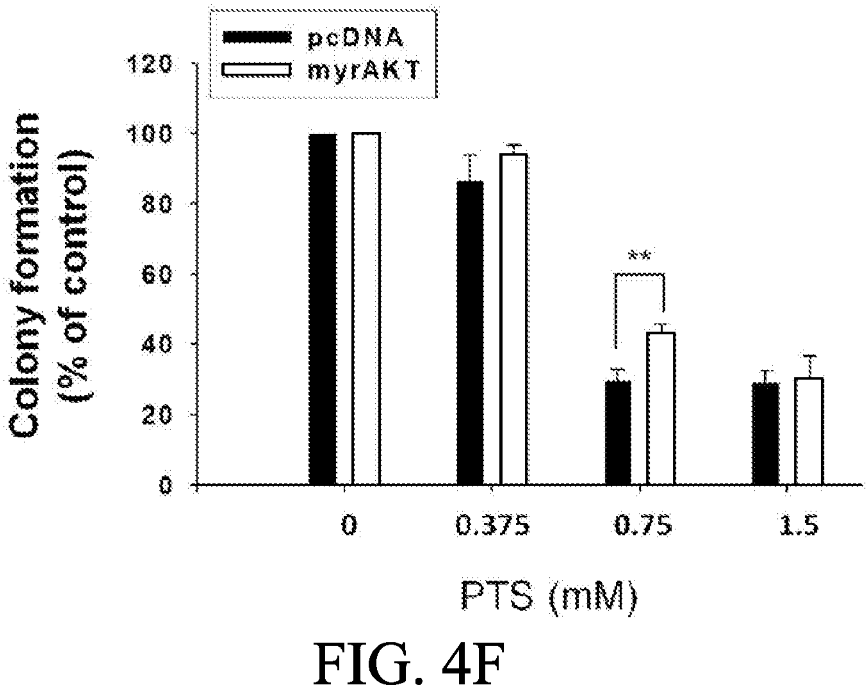

To further substantiate the role of Akt, the Myr-Akt overexpressed PC-3 cells were prepared with the method shown as follows. The plasmid encoding Myr-Akt, an N-terminally myristoylation signal-attached Akt, was a gift from Professor Mien-Chie Hung (The University of Texas, M. D. Anderson Cancer Center). For transfection, PC-3 cells were seeded into 60-mm tissue culture dishes with 30% confluence and grown for 24 h to 50-60% confluence. Each dish was washed with serum-free Opti-MEM (Life Technologies), and 2 ml of the serum-free Opti-MEM was then added. Aliquots containing Myr-Akt expression vector or a control plasmid in serum-free Opti-MEM were transfected into cells using Lipofectamine 2000 (Invitrogen) following the manufacturer's instructions. After incubation for 6 h at 37° C., cells were washed with serum-free Opti-MEM and incubated in 10% FBS-containing RPMI-1640 medium for 48 h. The cells were treated with or without p-TSA and then the related analyses were performed. As shown in FIGS. 4A to 4D, overexpression of constitutively active Myr-Akt in PC-3 cells significantly rescued the inhibitory effects on both mTOR and 4E-BP1 phosphorylation, and suppressed the activation of caspase-3 and cleavage of downstream substrate PARP-1. Furthermore, the functional rescue of Myr-Akt was determined. The data showed that overexpression of constitutively active Myr-Akt in PC-3 cells moderately but significantly blunted PTS-mediated growth inhibition using both SRB assay and colony formation assay (FIG. 4E and FIG. 4F); the IC50 values were significantly shifted from 1.97±0.01 to 2.18±0.10 mM ($P<0.05$) and 0.58±0.02 to 0.68±0.02 mM ($P<0.01$), respectively. However, overexpression of Myr-Akt had minimal effect on p-TSA-induced cyclin D1 down-regulation. The data suggested that Akt serves as a key player of mTOR translational pathway other than the regulation of cyclin D1 dynamics.

From the above, it could be seen that p-TSA inhibited the activation of Akt/mTOR/p70S6K pathway.

Example 4: Examination of the Effect of Lipid Raft and Cholesterol on p-TSA Action Lipid rafts are plasma membranes of cells containing glycosphingolipids and a number of receptors arranged in specific glycolipoprotein microdomains which serve as organizing centers to gather signaling molecules, membrane fluid and protein trafficking for a variety of cellular processes [31]. It has been suggested that several raft-associated signaling pathway components, including Akt, mTOR and p70S6K, involve in the regulation of cell survival [32]. To examine the effect of lipid raft on p-TSA action, lipid rafts were isolated from whole cells by sucrose gradient fractionation with subsequent analysis of several serine/threonine kinases localization in raft fractions by immunoblotting. The detailed method for lipid raft isolation was performed as follows.

Lipid rafts were isolated using lysis conditions and centrifugation on discontinuous sucrose gradients. Briefly, after the treatment of cells with or without p-TSA, the cells were washed with ice-cold PBS and lysed for 30 min on ice with 1% Triton X-100 in TNEV buffer (10 mM Tris-HCl, pH 7.5, 150 mM NaCl, 5 mM EDTA, 1 mM $Na_3VO_4$ and 1 mM PMSF). Cells were homogenized with 15 strokes with a Biovision tissue homogenizer. After centrifuging at 200 g for 8 min, the nuclei and cellular debris were pelleted and 400 μl supernatant was mixed with 400 μl 85% (w/v) sucrose in TNEV buffer, and then transferred to the bottom of a Beckman 13×51 mm centrifuge tube. The diluted lysate was overlaid with 2.4 ml 35% (w/v) sucrose in TNEV buffer and finally 1.4 ml 5% (w/v) sucrose in TNEV buffer. The samples were centrifuged in an SW55 rotor at 200,000 g for 18 h at 4° C. in a Beckman Optima L100K ultracentrifuge (Beckman Instruments, Palo Alto, CA, United States). Then, fractions in each volume of 350 μl were collected from the top gradient. 15 μl of each fraction was subjected to Western blot analysis to determine the location of target proteins in the discontinuous sucrose gradient.

Figure 5A:
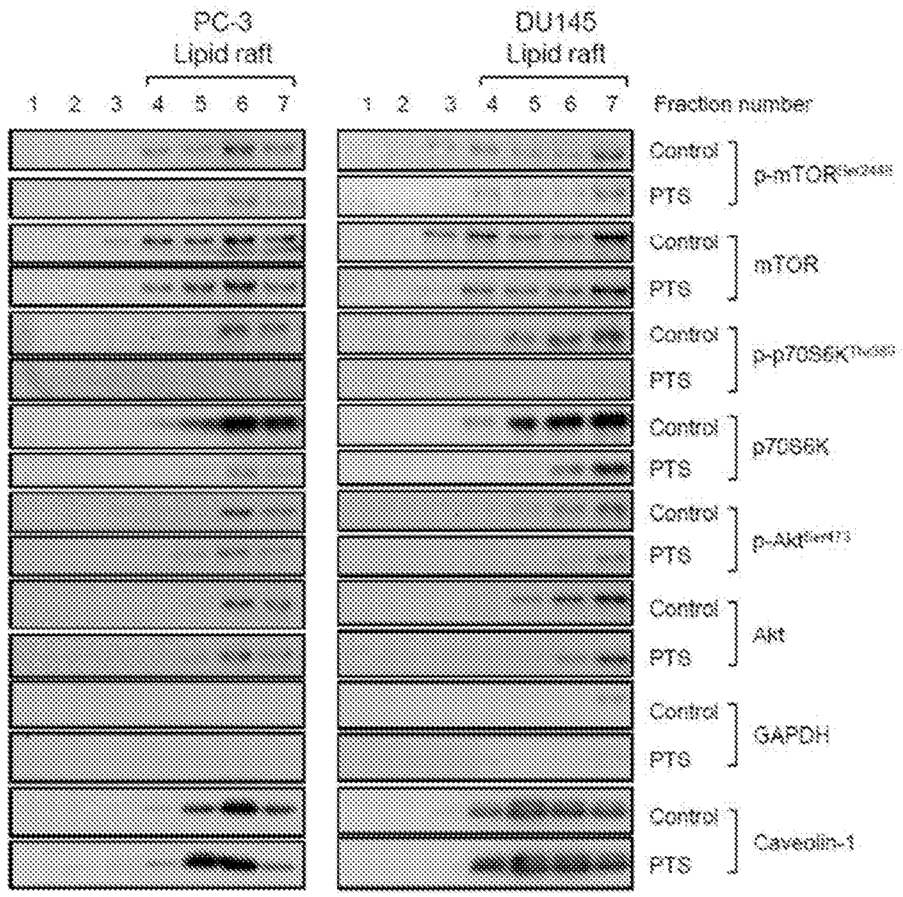
FIGS. 5A to 5C show the effect of p-TSA on lipid raft-associated expressions of several kinases.
Figure 5B:
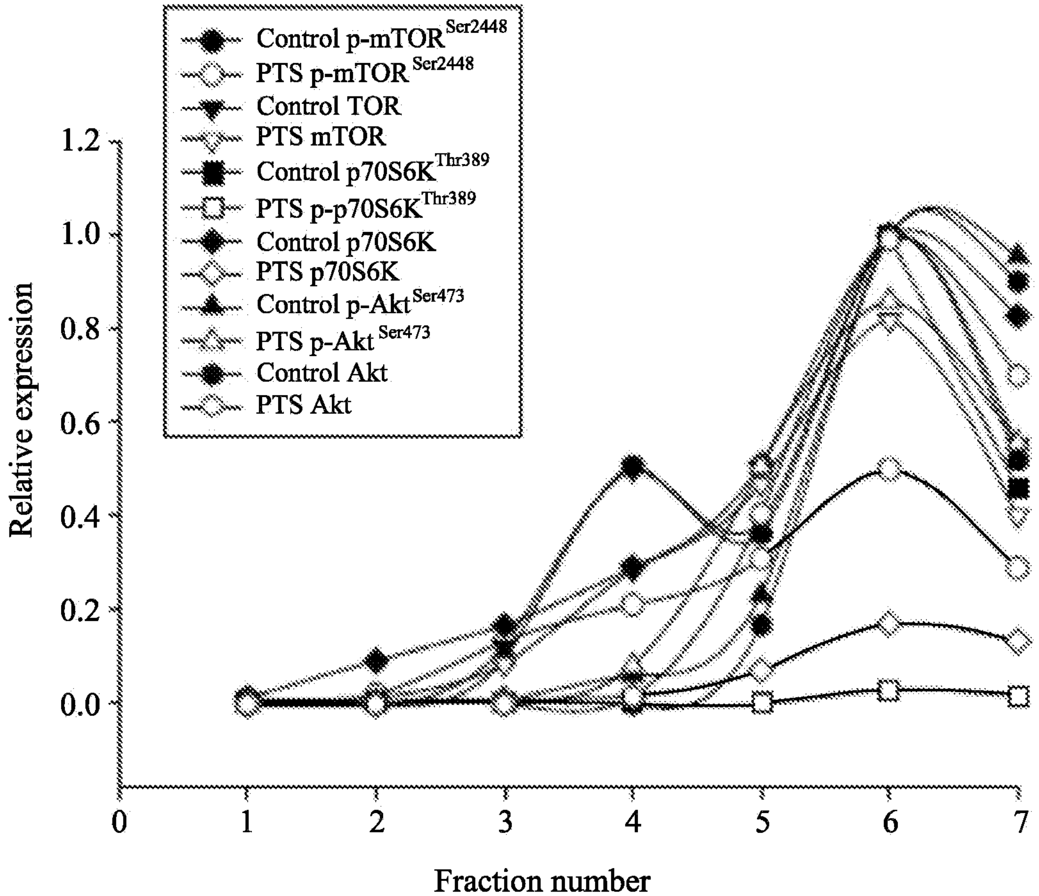
Figure 5C:
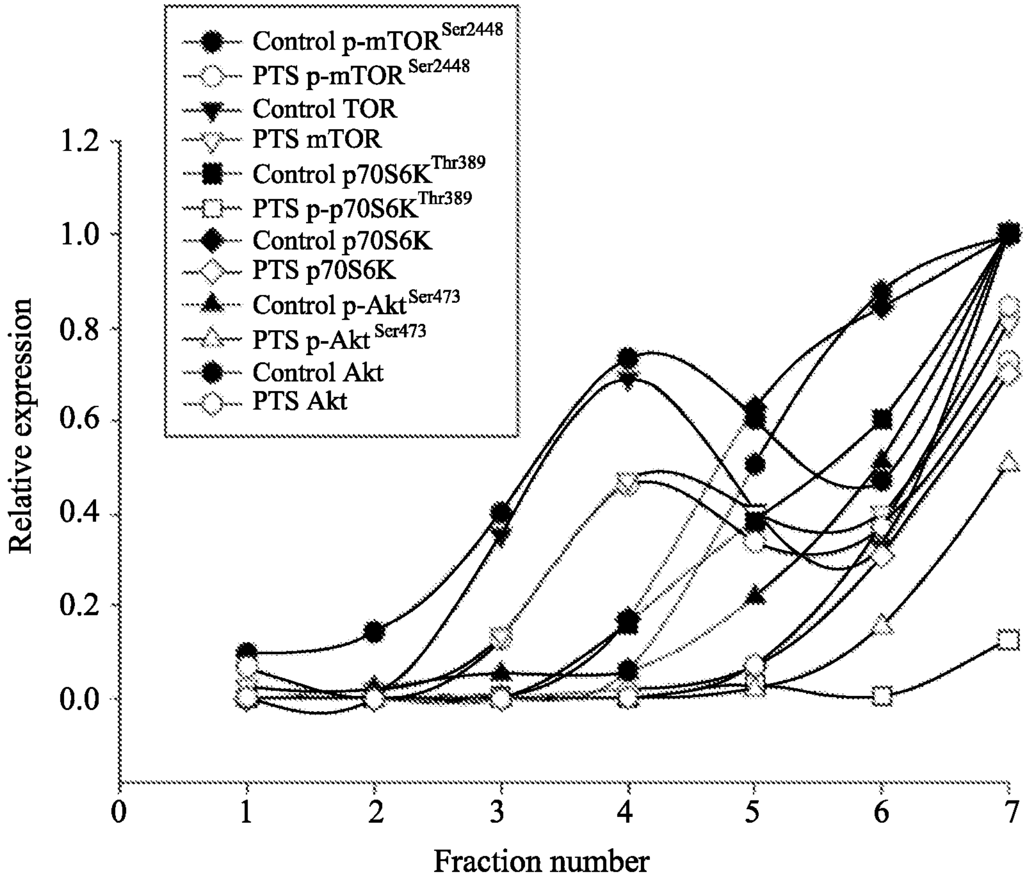

Results were shown in FIGS. 5A, 5B and 5C. The data showed that both PC-3 and DU-145 cell lines expressed all three raft-associated kinases with varied levels in which p70S6Ks were the most abundant. In addition, p-TSA led to decreased expressions of both raft-associated total and phosphorylated kinases in which the phosphorylated p70S6K expressions were completely abolished in both PC-3 and DU-145 cell lines.

Figure 6A:
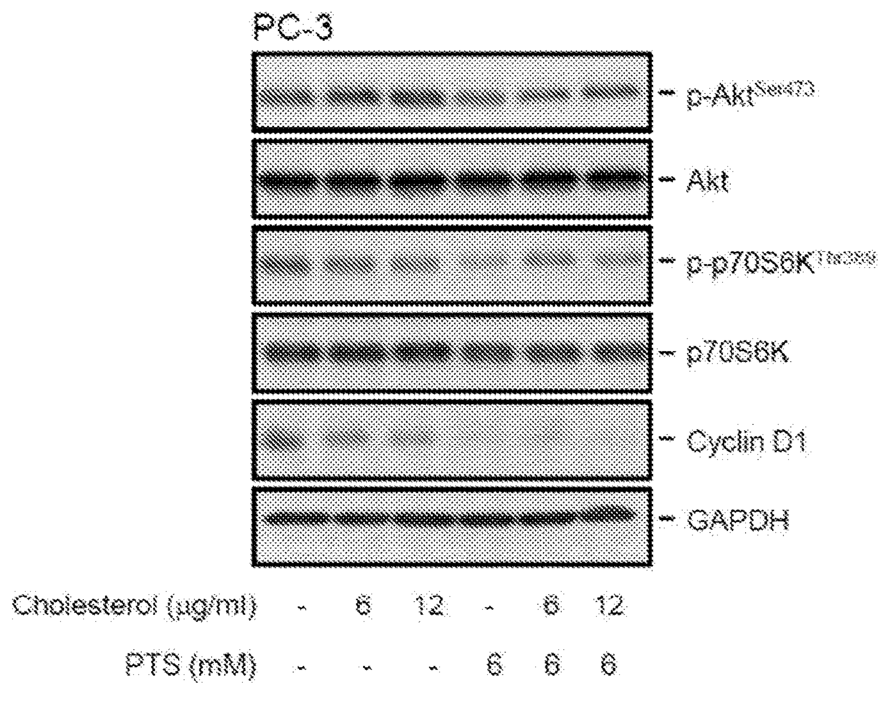
FIGS. 6A to 6E show the effect of cholesterol supplement on p-TSA-mediated effects. PC-3 and DU-145 cells were incubated in the absence or presence of the indicated agent for 1 h. After treatment, the cells were harvested and lysed for the detection of protein expressions by Western blot analysis (FIGS. 6A and 6C). The expression was quantified using Image Lab Software 6.0 (BIO-RAD) (FIGS. 6B and 6D). PC-3 cells were incubated in the presence of the indicated agent (PTS, 1.5 mM) for 10 days. After treatment, cells were fixed and stained for colony formation assay (FIG. 6E). Data are expressed as mean±SEM of three determinations. * $P<0.05$,  $P<0.01$ and * $P<0.001$ compared with p-TSA alone.
Figure 6B:
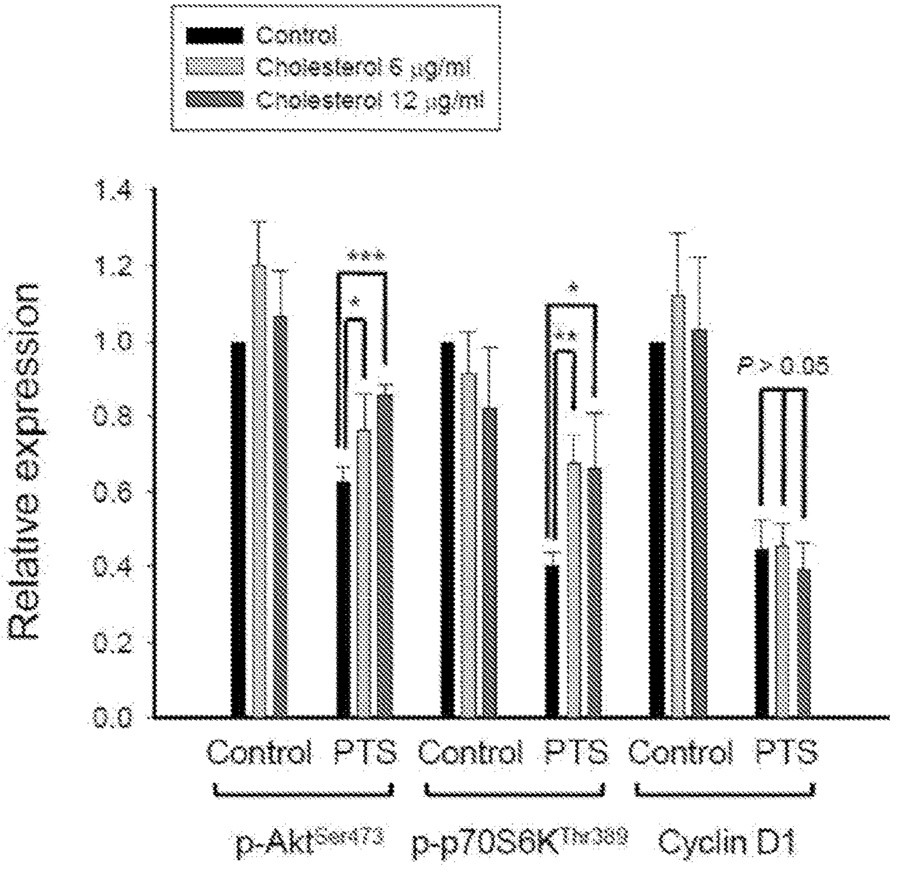
Figure 6C:
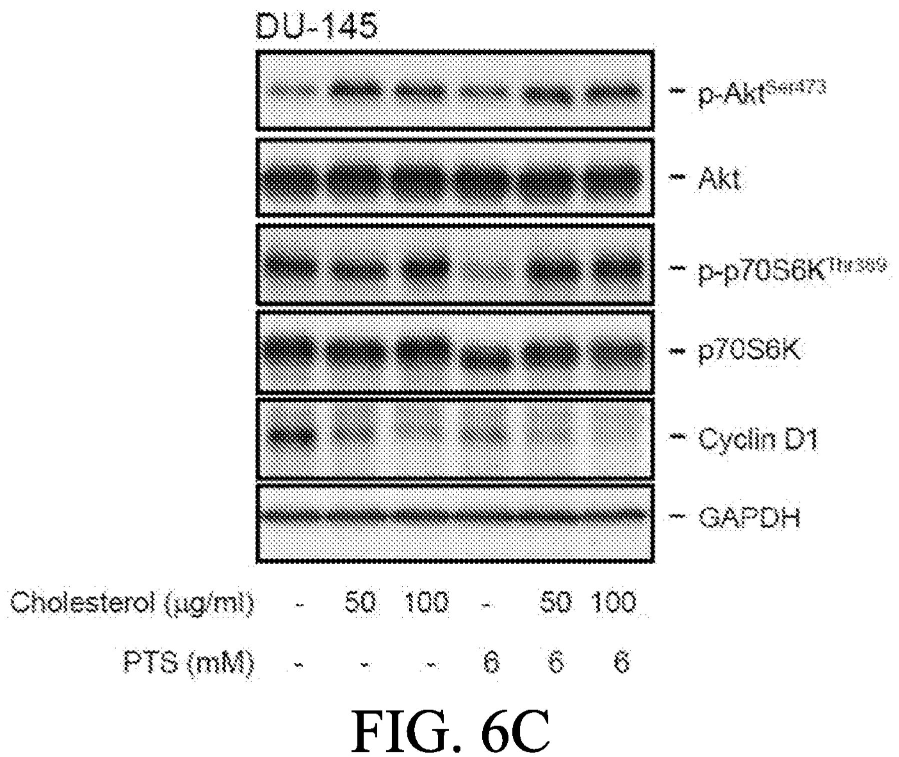
Figure 6D:
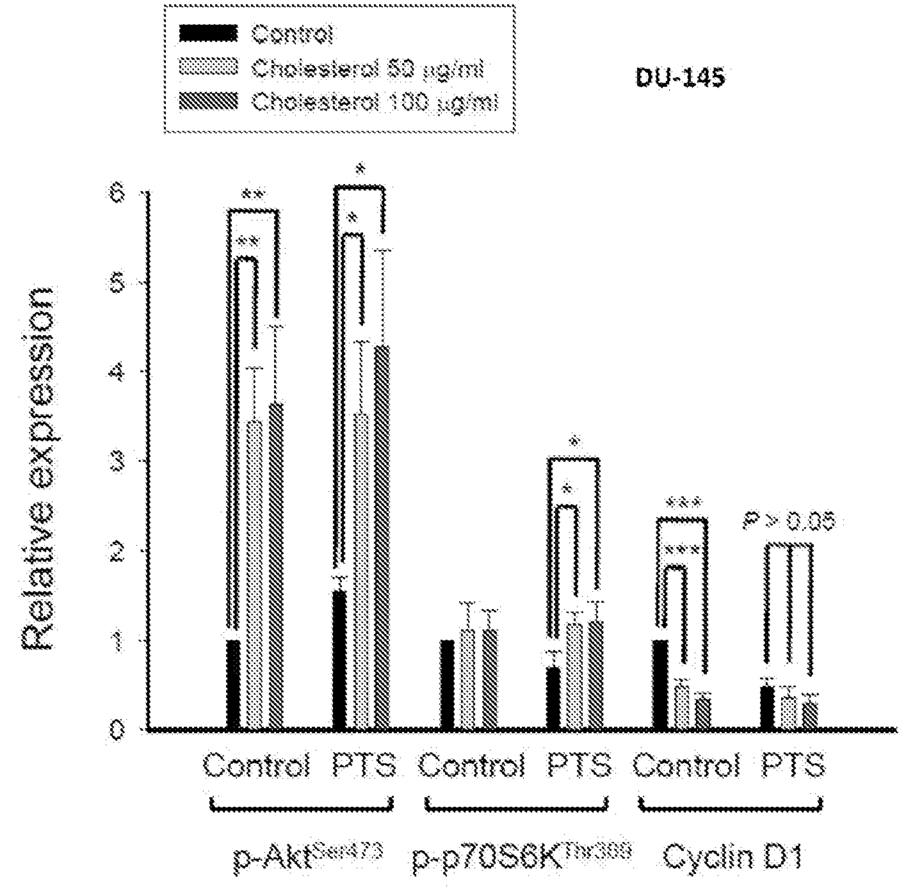
Figure 6E:
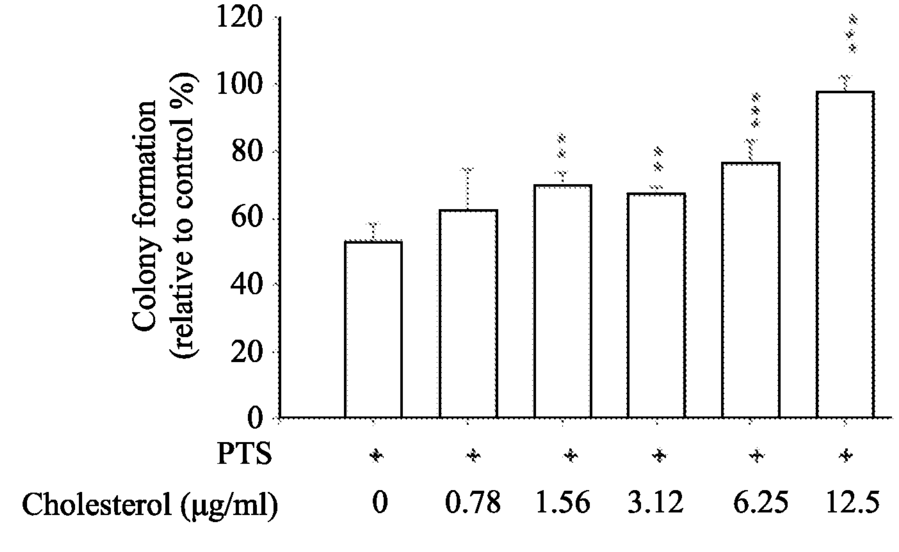

Moreover, cholesterol, a unique lipid molecule biosynthesized by all animal cells, is an essential structural constituent in cell membranes to maintain their structural integrity and fluidity. Rafts are composed of sphingolipids and cholesterol in outer exoplasmic leaflet, connected to phospholipids and cholesterol in inner cytoplasmic leaflet of the lipid bilayer [33, 34]. Recent studies have revealed that cholesterol depletion from lipid rafts is involved in apoptosis of several cancers. To examine the effect of cholesterol on p-TSA action, cholesterol was supplied to the p-TSA treated PC-3 and DU-145 cells. Results were shown in FIGS. 6A to 6D, and the data revealed that proper concentrations of cholesterol supplement significantly rescued p-TSA-induced decrease of Akt and p70S6K phosphorylation, but not cyclin D1 in both PC-3 and DU-15 cells. Cholesterol, by itself, induced an increase of Akt phosphorylation while a decrease of cyclin D1 protein expression particularly in DU-145 cells. Also, the functional rescue of cholesterol in cell growth was determined, and the results were shown in FIG. 6E. The data showed that cholesterol significantly rescued PTS-induced inhibition of cell growth using colony formation assay.

From the above, it could be seen that lipid raft and cholesterol are crucial to the activities of several kinases to p-TSA action.

Example 5: Examination of the Effect of p-TSA Action in Mouse Xenograft Models In vivo anti-tumor study was performed as follows. PC-3-derived cancer xenografts in nude mice were used as an in vivo model. The nude mice were subcutaneously injected with PC-3 cells ($10^7$ cell/mouse). The tumors were measured every day. When the tumors reached a volume of 100 $mm^3$, the mice were divided into two groups (n=8-10), and compound treatment was initiated. p-TSA was dissolved in 15% 1-methyl-2-pyrrolidone (NMP). Vehicle (15% NMP) or p-TSA was given intraperitoneally every other day. The length (l) and width (w) of the tumor were measured, and tumor volume was calculated as $lw^2/2$. The protocols of the in vivo study were approved by the Animal Care and Use Committee at National Taiwan University. All animal procedures and protocols were approved by AAALAC-accredited facility. Data analysis was shown as follows. Data were presented as mean±standard error of the mean (SEM) for the indicated number of separate experiments. The statistical analysis was performed using one way analysis of variance (ANOVA) for multiple sample sets. Single comparisons of appropriate groups were done with Student's t-test. P-values less than 0.05 are statistically considered significant.

Figure 7A:
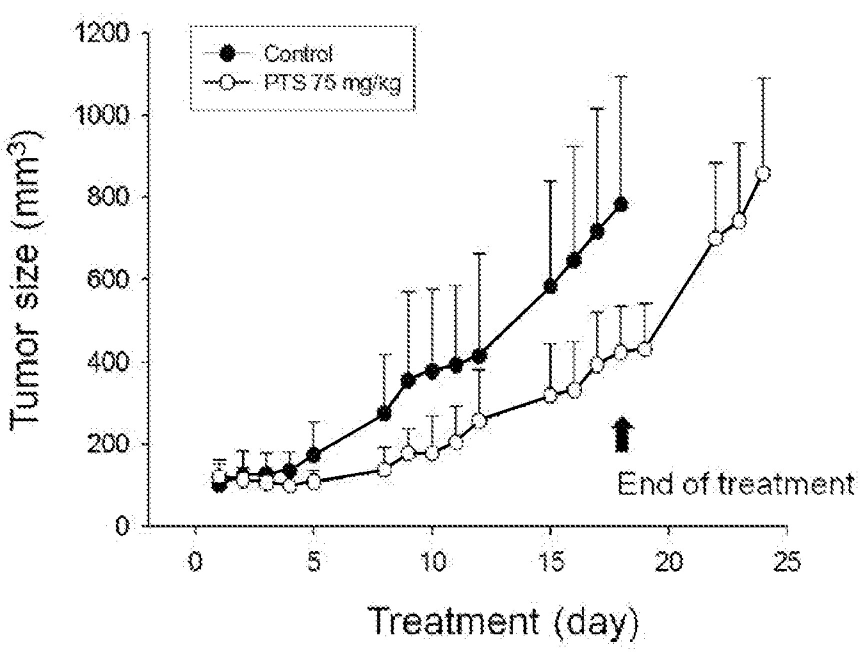
FIGS. 7A to 7D show the effect of p-TSA in an in vivo anti-tumor xenograft model. The nude mice were subcutaneously injected with PC-3 cells ($10^7$ cell/mouse). The tumors were measured every day. When the tumors reached a volume of 100 $mm^3$, the mice were divided into two groups and intraperitoneal p-TSA injection was initiated. The length (l) and width (w) of the tumor were measured, and the tumor volume was calculated as $lw^2/2$ (FIGS. 7A and 7B). The body weight was also measured (FIG. 7C). The protocols of the in vivo study were approved by the Animal Care and Use Committee at National Taiwan University. All animal procedures and protocols were approved by Association for Assessment and Accreditation of Laboratory Animal Care International (AAALAC)-accredited facility. The p-Akt expression of randomly selected six tumors in both control and PTS groups has been detected (FIG. 7D). Data are expressed as mean±SD.
Figure 7B:
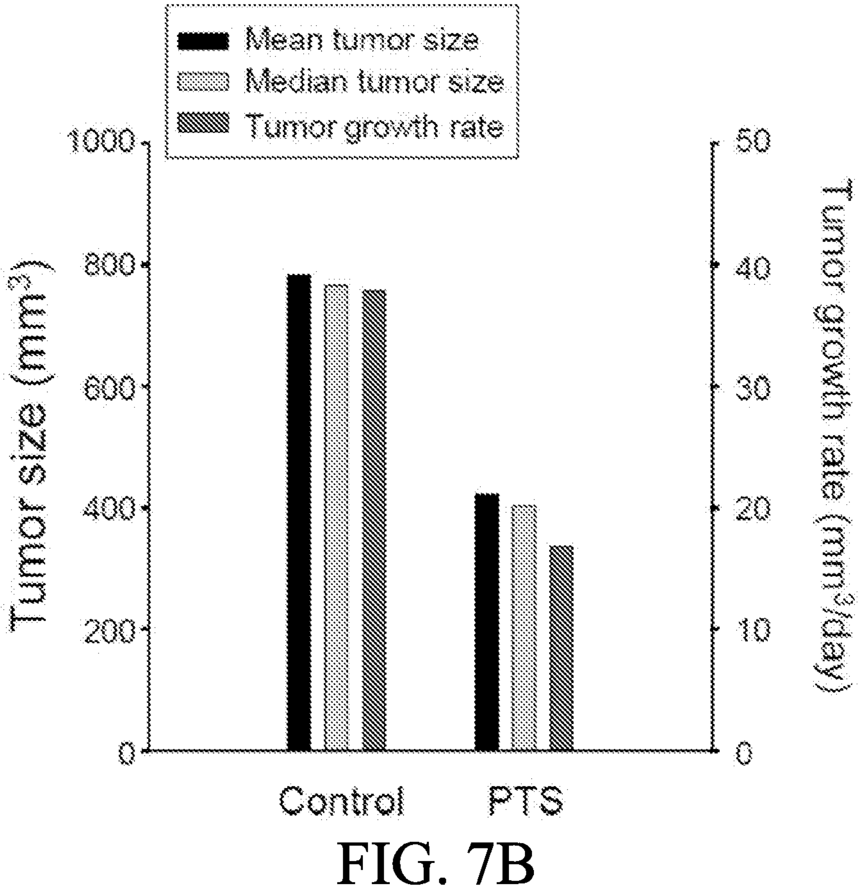
Figure 7C:
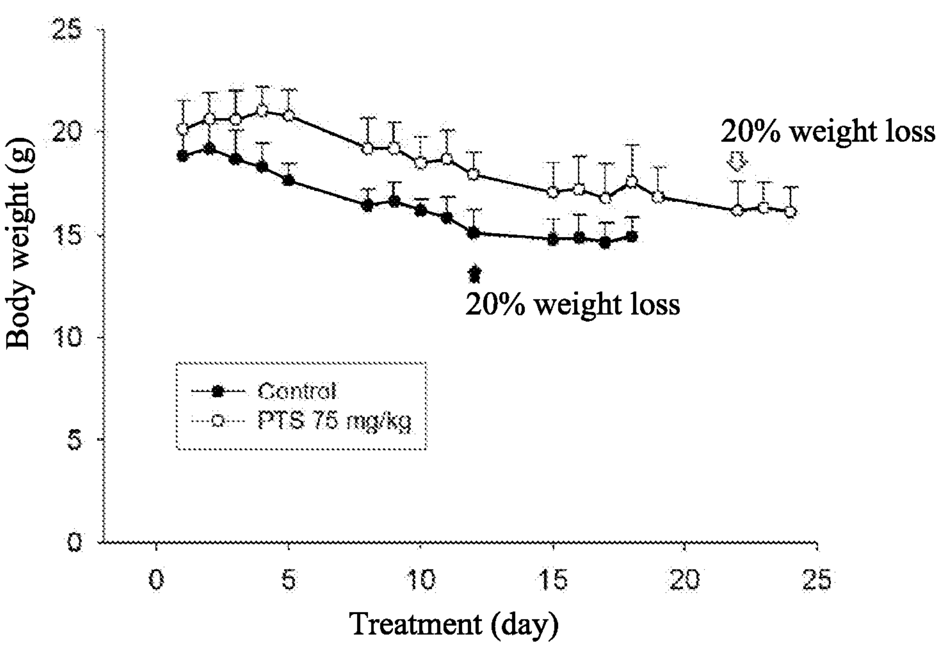
Figure 7D:
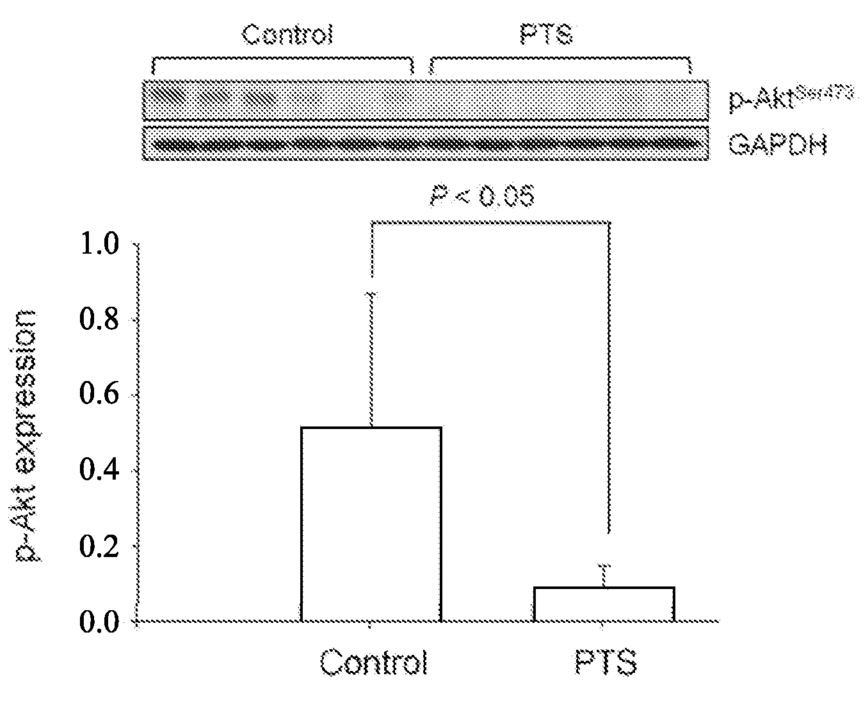

The tumor xenograft in nude mice models after subcutaneously inoculated PC-3 cells was used to conduct in vivo efficacy evaluation of p-TSA. The operator was fully blinded to the experimental treatment. The initial intraperitoneal injection of 75 mg/kg p-TSA was given when the tumor reached a size of 100 $mm^3$ (p-TSA group 121±40 $mm^3$ v.s. control group 101±48 $mm^3$). First, the tumor growth inhibition treatment/control (T/C) ratio was used to quantify the treatment effect of p-TSA in the mouse xenograft model. As shown in FIG. 7A, the data demonstrated that the tumor growth inhibition T/C ratio was 0.44 at the end of p-TSA treatment. In addition, cessation of p-TSA treatment caused a rebounded growth of tumor, suggesting that p-TSA was fully responsible to the inhibition of tumor growth. In addition, as shown in FIG. 7B, the growth rates of control group v.s. p-TSA group were 37.8 $mm^3$/day v.s. 16.8 $mm^3$/day, indicating a 56% inhibition by p-TSA. The median tumor size of p-TSA group was 403 $mm^3$ compared to 765 $mm^3$ in the control group, revealing a 47% inhibition by p-TSA. Furthermore, as shown in FIG. 7C, in vivo study showed a progressive loss of body weight in both control and p-TSA groups, although no significant between-group difference was shown. It also demonstrated that the control group reached to a 20% loss of body weight on the $12^{th}$ day compared to the $22^{th}$ in p-TSA group. Moreover, as shown in FIG. 7D, the detection of p-Akt expression in tumors also showed a significant inhibitory effect of PTS.

From the above, it could be seen that p-TSA displayed in vivo efficacy of anti-CRPC in mouse xenograft models.

Autonomous cell proliferation, one of the hallmarks of cancer cells, is driven by activated survival- and growth-promoting oncogenes. Phosphatidylinositol-3-kinase (PI3K)/Akt/mTOR/p70S6K signaling pathway is commonly activated pathways in prostate cancer cells. Loss of the PTEN tumor suppressor is frequently reported factors in aberrant activation of this pathway implicated not only in survival and growth of prostate cancer cells but also in tumor metastasis [5, 36, 37]. As such, inactivation of these pathways may have opportunities for the therapy of prostate cancer. Some studies have reported promising preclinical results of PI3K inhibitors while the data from clinical trials were less convincing. Accordingly, dual PI3K/mTOR inhibitors that block both PI3K/Akt and mTOR have been proposed to achieve better anticancer outcomes [36, 38]. However, prostate cancer which shows a wide variety of biological and clinical behavior represents the epiphenomenon of an extreme genetic heterogeneity [37]. The examination of multiple specific molecular alterations and the development of the most appropriate therapy based on the multiple factors may provide better opportunities for therapy.

The present disclosure has targeted CRPC by using both PC-3 and DU-145 cell lines to elaborate p-TSA-mediated multiple mechanisms that efficiently block the growth and survival of the cells both in vitro and in vivo. p-TSA displayed an effective and long-term stable anti-proliferative activity through induction of G1 phase that ultimately induced cell apoptosis. Typically, DNA damage or certain cellular stresses tend to cause G1 checkpoint arrest to allow the repair of damage to rescue cells from programmed cell death. However, p-TSA induced mitochondrial damage, indicating that the cellular impairment was not significantly repaired during the p-TSA treatment that ultimately led to apoptosis. The integrity and permeability of mitochondrial membrane are critically regulated by Bcl-2 family of proteins [26]. PUMA is a p53-dependent and p53-independent pro-apoptotic member of the BH3-only subgroup of Bcl-2 family and has been identified to directly bind anti-apoptotic Bcl-2 members through its BH3 domain which induces the activation of pro-apoptotic Bcl-2 members and an increase of outer mitochondrial membrane permeability, leading to mitochondrial dysfunction and caspase activation [39]. Recently, several lines of evidence suggest that PUMA, similar to Bim, Noxa, and tBid, are direct Bak activators to initiate oligomerization and activation of Bak [40]. p-TSA significantly induced a significant increase in expressions of PUMA and Bak, suggesting their contribution to mitochondrial dysfunction. p-TSA also significantly inhibited Mcl-1 expression in DU-145 cells. It has been reported that Mcl-1 and PUMA co-localize at the mitochondria and Mcl-1 level can be increased during the co-expression with PUMA, indicating that PUMA can stabilize Mcl-1. In contrast, several studies have revealed that the binding of PUMA to Mcl-1 is not sufficient to prevent rapid degradation of Mcl-1 [41]. Our data showed similar results that PUMA did not prevent Mcl-1 degradation and, furthermore, mitochondrial dysfunction was partially attributed to Mcl-1 degradation in DU-145 cells.

During G1 phase, cells grow in size with intense synthesis of mRNA and proteins for DNA synthesis in which mTOR plays a key role through induction of phosphorylation and activation of several downstream translation factors [28-30]. p-TSA markedly inhibited mTOR phosphorylation in Ser2448 within a C-terminal regulatory region, a crucial marker of mTOR activation [28, 42]. This phosphorylation can be activated through either Akt-dependent or -independent pathway [42, 43]. The overexpression of Myr-Akt, a constitutively active form of Akt, almost completely abolished p-TSA-mediated inhibition of phosphorylation at both mTORSer2448 and 4E-BP1Thr37/46 (a direct substrate of mTOR) in PC-3 cells, suggesting the inhibition of Akt-dependent mTOR activity to p-TSA action. In contrast, the fact that Akt activity in DU-145 cells was not apparent might be due to the presence of PTEN, a negative regulator of PI3K/Akt activity, because DU-145 other than PC-3 expresses PTEN at both mRNA and protein levels [44]. The regulation of mTOR activity through Akt-independent pathway in DU-145 cells has been discussed below.

Cyclin D1 is a key regulator in G1 phase of cell cycle progression, and aberrant cyclin D1 expression is implicated in tumorigenesis, metastasis and tumor progression in many human neoplasms [45, 46]. Cyclin D1 overexpression has been implicated in prostate carcinogenesis and aggravated bone metastasis [45]. p-TSA induced G1 arrest of the cell cycle and efficiently blocked the expression of cyclin D1 in both bone metastasis-derived PC-3 and brain metastasis-derived DU-145 cells, indicating the potential of p-TSA on the inhibition of metastasis in prostate cancers. However, the Myr-Akt overexpression did not rescue the cyclin D1 down-regulation, indicating the existence of Akt-independent regulatory pathways. Several pathways have been proposed to be involved in cyclin D1 down-regulation, including the reduction of cellular ATP levels, activation of protein kinase C and phosphatase PP2A, depletion of adenine nucleotide translocase 2 and down-regulation of c-Myc [47-49]. The clear pathway needs further elucidation. p-TSA-induced G1 arrest of the cell cycle was independent of p21 and p27. Similar effects have been reported in a number of studies. Vaziri et al. reported that butyrate-induced G1 arrest occurred in primary cultures of fibroblasts from transgenic p21 "knockout" mice (p21−/−), indicating the independency of p21 induction [50]. Berns et al. reported that a dominant negative mutant of c-Myc could induce G1 arrest of the cell cycle mouse in embryo fibroblasts deficient for both p27 and p21 [51]. These studies support that both p21 and p27 are not rate-limiting cell cycle regulators to p-TSA-mediated G1 arrest.

Recently, much attention has been paid to the function of lipid raft in anticancer research since raft-associated signaling pathway components, including Akt, mTOR and p70S6K, which have been implicated in cell survival regulation [32]. It is of importance in dealing with prostate cancer because prostate cancer cells contain more lipid rafts [34, 52]. Cholesterol is essential in keeping membrane integrity and fluidity and is crucial for raft/caveolae formation. The changes of cholesterol contents of cells can modify the properties of lipid rafts [53] and cholesterol depletion from the plasma membrane induces apoptosis, in particular in prostate cancer cells that have higher membrane cholesterol contents [52]. Therefore, the therapy with target for rafts/cholesterol would be a potential strategy. The data demonstrated that both PC-3 and DU-145 cell lines expressed raft-associated Akt, mTOR and p70S6K. p-TSA induced decreases of these expressions of both total and phosphorylated forms. Several studies suggest that the integrity of lipid rafts is necessary to the activities of these kinases. Disturbance or disruption of the lipid raft is able to impair the phosphorylation of these kinases [54-56]. Therefore, p-TSA might cause the disturbance or disruption of lipid raft, leading to the dissociation and inactivation of these kinases. The supplement of cholesterol significantly rescued p-TSA-induced inactivation of these kinases and further linked the role of cholesterol on p-TSA-mediated raft disruption. However, cholesterol supplement did not prevent the down-regulation of cyclin D1 because it was not raft-associated component. The data also supported the notion that cyclin D1 down-regulation was not a downstream event of the Akt/mTOR/p70S6K pathway. Finally, the nude mice xenograft model was used to examine the in vivo anti-tumor efficacy of p-TSA. The intraperitoneal treatment of p-TSA induced a 56% inhibition of tumor growth through the measurement of T/C and growth rate and a 47% inhibition by detecting the median tumor size. Akt phosphorylation in tumors also was significantly inhibited by PTS. The data revealed an in vivo efficacy of p-TSA.

In conclusion, the data suggest that p-TSA is an effective anti-tumor agent with both in vitro and in vivo efficacies. p-TSA induced anti-proliferative effect through an arrest of the cell cycle at G1 phase and apoptosis via Bak- and PUMA-involved mitochondrial dysfunction in both PC-3 and DU-145 cells. Furthermore, Akt is critical to mTOR/p70S6K pathway in the apoptotic regulation in PTEN null/Akt active PC-3 cells but not in PTEN wild-type DU-145 cells. Disturbance of lipid raft and cholesterol contents may, at least partly, explain the dissociation and inactivation of Akt, mTOR and p70S6K in both cell lines.

The disclosure has been described using exemplary embodiments. However, it is to be understood that the scope of the disclosure is not limited to the disclosed embodiments. On the contrary, it is intended to cover various modifications and similar rearrangement. The scope of the claims therefore should be accorded to the broadest interpretation so as to encompass all such modifications and similar arrangements.

REFERENCES

[1] R. M. Mohammad, I. Muqbil, L. Lowe, C. Yedjou, H. Y. Hsu, L. T. Lin, M. D. Siegelin, C. Fimognari, N. B. Kumar, Q. P. Dou, H. Yang, A. K. Samadi, G. L. Russo, C. Spagnuolo, S. K. Ray, M. Chakrabarti, J. D. Morre, H. M. Coley, K. Honoki, H. Fujii, A. G. Georgakilas, A. Amedei, E. Niccolai, A. Amin, S. S. Ashraf, W. G. Helferich, X. Yang, C. S. Boosani, G Guha, D. Bhakta, M. R. Ciriolo, K. Aquilano, S. Chen, S. I. Mohammed, W. N. Keith, A. Bilsland, D. Halicka, S. Nowsheen, A. S. Azmi, Broad targeting of resistance to apoptosis in cancer. Semin Cancer Biol. 35 Suppl (2015) S78-103.

[2] V. Velcheti, S. Karnik, S. F. Bardot, O. Prakash, Pathogenesis of prostate cancer: lessons from basic research. Ochsner. J. 8 (2008) 213-218.

[3] M. Marcelli, M. Ittmann, S. Mariani, R. Sutherland, R. Nigam, L. Murthy, Y. Zhao, D. DiConcini, E. Puxeddu, A. Esen, J. Eastham, N. L. Weigel, D. J. Lamb, Androgen receptor mutations in prostate cancer. Cancer Res. 60 (2000) 944-999.

[4] C. D. Chen, D. S. Welsbie, C. Tran, S. H. Baek, R. Chen, R. Vessell, M. G. Rosenfeld, C. L. Sawyers, Molecular determinants of resistance to antiandrogen therapy. Nat. Med. 10 (2004) 33-39.

[5] K. A. Cohen-Solal, R. K. Boregowda, A. Lasfar, RUNX2 and the PI3K/AKT axis reciprocal activation as a driving force for tumor progression. Mol. Cancer 14 (2015) 137.

[6] J. A. McCubrey, S. L. Abrams, T. L. Fitzgerald, L. Cocco, A. M. Martelli, G Montalto, M. Cervello, A. Scalisi, S. Candido, M. Libra, L. S. Steelman, Roles of signaling pathways in drug resistance, cancer initiating cells and cancer progression and metastasis. Adv. Biol. Regul. 57 (2015) 75-101.

[7] W. J. Leu, ShP. Swain, S. H. Chan, J. L. Hsu, S. P. Liu, M. L. Chan, C. C. Yu, L. C. Hsu, Y. L. Chou, W. L. Chang, D. R. Hou, J. H. Guh, Non-immunosuppressive triazole-based small molecule induces anticancer activity against human hormone-refractory prostate cancers: the role in inhibition of PI3K/AKT/mTOR and c-Myc signaling pathways. Oncotarget 7 (2016) 76995-77009.

[8] M. E. McMenamin, P. Soung, S. Perera, I. Kaplan, M. Loda, W. R. Sellers, Loss of PTEN expression in paraffin-embedded primary prostate cancer correlates with high Gleason score and advanced stage. Cancer Res. 59 (1999) 4291-4296.

[9] S. Shukla, M. Shukla, G T. MacLennan, P. Fu, S. Gupta, Deregulation of FOXO3A During Prostate Cancer Progression. Int. J. Oncol. 34 (2009) 1613-1620.

[10] C. Zerbinati, L. Iuliano, Cholesterol and related sterols autoxidation. Free. Radic. Biol. Med. 111 (2017) 151-155.

[11] J. P. Incardona, S. Eaton, Cholesterol in signal transduction. Curr. Opin. Cell Biol. 12 (2000) 193-203.

[12] E. Sezgin, I. Levental, S. Mayor, C. Eggeling, The mystery of membrane organization: composition, regulation and roles of lipid rafts. Nat. Rev. Mol. Cell Biol. 18 (2017) 361-374.

[13] C. Gajate, F. Mollinedo, Lipid raft-mediated Fas/CD95 apoptotic signaling in leukemic cells and normal leukocytes and therapeutic implications. J. Leukoc. Biol. 98 (2015) 739-759.

[14] R. Yamaguchi, G Perkins, K. Hirota, Targeting cholesterol with β-cyclodextrin sensitizes cancer cells for apoptosis. FEBS Lett. 589 (2015) 4097-4105.

[15] K. Motoyama, K Kameyama, R. Onodera, N. Araki, F. Hirayama, K. Uekama, H. Arima, Involvement of PI3K-Akt-Bad pathway in apoptosis induced by 2,6-di-O-methyl-beta-cyclodextrin, not 2,6-di-O-methyl-alpha-cyclodextrin, through cholesterol depletion from lipid rafts on plasma membranes in cells. Eur. J. Pharm. Sci. 38 (2009) 249-261.

[16] F. C. Huang, The critical role of membrane cholesterol in *salmonella*-induced autophagy in intestinal epithelial cells. Int. J. Mol. Sci. 15 (2014) 12558-12572.

[17] Y. C. Li, M. J. Park, S. K. Ye, C. W. Kim, Y N Kim, Elevated levels of cholesterol-rich lipid rafts in cancer cells are correlated with apoptosis sensitivity induced by cholesterol-depleting agents. Am. J. Pathol. 168 (2006) 1107-1118.

[18] Y. Gao, Y. Gao, W. Guan, L. Huang, X. Xu, C. Zhang, X. Chen, Y. Wu, G Zeng, N. Zhong, Antitumor effect of para-toluenesulfonamide against lung cancer xenograft in a mouse model. J. Thorac. Dis. 5 (2013) 472-483.

[19] Z. Liu, C. Liang, Z. Zhang, J. Pan, H. Xia, N. Zhong, L. Li, Para-toluenesulfonamide induces tongue squamous cell carcinoma cell death through disturbing lysosomal stability. Anticancer Drugs. 26 (2015) 1026-1033.

[20] Q. He, A. R. Kuang, Y. S. Guan, Y. Q. Liu, Puncture injection of para-toluenesulfonamide combined with chemoembolization for advanced hepatocellular carcinoma. World J. Gastroenterol. 18 (2012) 6861-6864.

[21] J. He, W. Ying, H. Yang, X. Xu, W. Shao, Y. Guan, M. Jiang, Y. Wu, B. Zhong, D. Wang, S. Tucker, N. Zhong, Gemcitabine plus cisplatin chemotherapy with concurrent para-toluenesulfonamide local injection therapy for peripherally advanced nonsmall cell lung cancer larger than 3 cm in the greatest dimension. Anticancer Drugs. 20 (2009) 838-844.

[22] J. H. Guh, T. L. Hwang, F. N. Ko, S. C. Chueh, M. K. Lai, C. M. Teng, Antiproliferative effect in human prostatic smooth muscle cells by nitric oxide donor. Mol. Pharmacol. 53 (1998) 467-474.

[23] H. A. Arango, S. Icely, W. S. Roberts, D. Cavanagh, J. L. Becker, Aspirin effects on endometrial cancer cell growth. Obstet. Gynecol. 97 (2001) 423-427.

[24] J. C. Lee, L. C. Chung, Y. J. Chen, T. H. Feng, W. T. Chen, H. H. Juang, Upregulation of B-cell translocation gene 2 by epigallocatechin-3-gallate via p38 and ERK signaling blocks cell proliferation in human oral squamous cell carcinoma cells. Cancer Lett. 360 (2015) 310-318.

[25] R. Moreno-Sanchez, S. Rodriguez-Enriquez, A. Marin-Hernandez, E. Saavedra, Energy metabolism in tumor cells. FEBS J. 274 (2007) 1393-1418.

[26] Y. Tsujimoto, Cell death regulation by the Bcl-2 protein family in the mitochondria. J. Cell. Physiol. 195 (2003) 158-167.

[27] O. Coqueret, Linking cyclins to transcriptional control. Gene. 299 (2002) 35-55.

[28] L. Asnaghi, P. Bruno, M. Priulla, A. Nicolin, mTOR: a protein kinase switching between life and death. Pharmacol. Res. 50 (2004) 545-549.

[29] T. R. Fenton, I. T. Gout, Functions and regulation of the 70 kDa ribosomal S6 kinases. Int. J. Biochem. Cell Biol. 43 (2011) 47-59.

[30] A. C. Gingras, S. G. Kennedy, M. A. O'Leary, N. Sonenberg, N. Hay, 4E-BP1, a repressor of mRNA translation, is phosphorylated and inactivated by the Akt(PKB) signaling pathway. Genes Dev. 12 (1998) 502-513.

[31] Sezgin E, Levental I, Mayor S, Eggeling C. The mystery of membrane organization: composition, regulation and roles of lipid rafts. Nat. Rev. Mol. Cell Biol. 18 (2017) 361-374.

[32] Y. Liu, J. Y. Lv, J. F. Shi, M. Yang, S. H. Liu, Z. W. Li, H. B. Wang, S. G. Zhang, Z. W. Liu, J. B. Ding, D. P. Xu, J. M. Zhao, Targeting the raft-associated Akt signaling in hepatocellular carcinoma. Biomed. Res. Int. 2014 (2014) 836025.

[33] K. Simons, R. Ehehalt, Cholesterol, lipid rafts, and disease. J. Clin. Invest. 110 (2002) 597-603.

[34] J. L. Hsu, J. H. Guh. Alterations in Cellular Cholesterol Content Can Be a Potential Anticancer Strategy. Biomed. J. Sci. Tech. Res. 1 (2017) 1-5.

[35] R. Onodera, K. Motoyama, A. Okamatsu, T. Higashi, R. Kariya, S. Okada, H. Arima, Involvement of cholesterol depletion from lipid rafts in apoptosis induced by methyl-β-cyclodextrin. Int. J. Pharm. 452 (2013) 116-123.

[36] C. M. Statz, S. E. Patterson, S. M. Mockus, mTOR Inhibitors in Castration-Resistant Prostate Cancer: A Systematic Review. Target Oncol. 12 (2017) 47-59.

[37] C. Ciccarese, E Massari, R. Iacovelli, M. Fiorentino, R. Montironi, V. Di Nunno, F. Giunchi, M. Brunelli, G Tortora, Prostate cancer heterogeneity: Discovering novel molecular targets for therapy. Cancer Treat. Rev. 54 (2017) 68-73.

[38] K. D. Tang, M. T. Ling, Targeting drug-resistant prostate cancer with dual PI3K/mTOR inhibition. Curr. Med. Chem. 21 (2014) 3048-3056.

[39] P. Hikisz, Z. M. Kiliańska, PUMA, a critical mediator of cell death—one decade on from its discovery. Cell. Mol. Biol. Lett. 17 (2012) 646-669.

[40] H. Dai, Y. P. Pang, M Ramirez-Alvarado, S. H. Kaufmann, Evaluation of the BH3-only protein Puma as a direct Bak activator. J. Biol. Chem. 289 (2014) 89-99.

[41] Y. Mei, W. Du, Y. Yang, M. Wu, Puma(*)Mcl-1 interaction is not sufficient to prevent rapid degradation of Mcl-1. Oncogene 24 (2005) 7224-7237.

[42] A. Sekulie, C. C. Hudson, J. L. Homme, P. Yin, D. M. Otterness, L. M. Karnitz, R. T. Abraham, A direct linkage between the phosphoinositide 3-kinase-AKT signaling pathway and the mammalian target of rapamycin in mitogen-stimulated and transformed cells. Cancer Res. 60 (2000) 3504-3513.

[43] G. G Chiang, R. T. Abraham, Phosphorylation of mammalian target of rapamycin (mTOR) at Ser-2448 is mediated by p70S6 kinase. J. Biol. Chem. 280 (2005) 25485-25490.

[44] D. R. Bastola, G S. Pahwa, M. F. Lin, P. W. Cheng, Downregulation of PTEN/MMAC/TEP1 expression in human prostate cancer cell line DU145 by growth stimuli. Mol. Cell. Biochem. 236 (2002) 75-81.

[45] M. Drobnjak, I. Osman, H. I. Scher, M. Fazzari, C. Cordon-Cardo, Overexpression of cyclin D1 is associated with metastatic prostate cancer to bone. Clin. Cancer Res. 6 (2000) 1891-1895.

[46] N. P. Fuste, R. Fernandez-Hernandez, T. Cemeli, C. Mirantes, N. Pedraza, M. Rafel, J. Torres-Rosell, N. Colomina, F. Ferrezuelo, X. Dolcet, E. Gari, Cytoplasmic cyclin D1 regulates cell invasion and metastasis through the phosphorylation of paxillin Nat. Commun. 7 (2016) 11581.

[47] L. Guan, K. Song, M. A. Pysz, K. J. Curry, A. A. Hizli, D. Danielpour, A. R. Black, J. D. Black, Protein kinase C-mediated down-regulation of cyclin D1 involves activation of the translational repressor 4E-BP1 via a phosphoinositide 3-kinase/Akt-independent, protein phosphatase 2A-dependent mechanism in intestinal epithelial cells. J. Biol. Chem. 282 (2007) 14213-14225.

[48] M. Watanabe M, Y. Iizumi Y, M. Sukeno M, M. Iizuka-Ohashi M, Y. Sowa Y, T. Sakai, The pleiotropic regulation of cyclin D1 by newly identified sesaminol-binding protein ANT2. Oncogenesis 6 (2017) e311.

[49] D. Amendola, M. De Salvo, R. Marchese, C. Verga Falzacappa, A. Stigliano, E. Carico, E. Brunetti, M. Moscarini, B. Bucci, Myc down-regulation affects cyclin D1/cdk4 activity and induces apoptosis via Smac/Diablo pathway in an astrocytoma cell line. Cell Prolif. 42 (2009) 94-109.

[50] C. Vaziri, L. Stice, D. V. Faller, Butyrate-induced G1 arrest results from p21-independent disruption of retinoblastoma protein-mediated signals. Cell Growth Differ. 1998 June; 9(6):465-74.

[51] K. Berns, C. Martins, J. H. Dannenberg, A. Berns, H. to Ridle, R. Bernards, p27kip1-independent cell cycle regulation by MYC. Oncogene. 2000 Oct. 5; 19(42): 4822-7.

[52] Y. C. Li, M. J. Park, S. K. Ye, C. W. Kim, Y. N. Kim, Elevated levels of cholesterol-rich lipid rafts in cancer cells are correlated with apoptosis sensitivity induced by cholesterol-depleting agents. Am. J. Pathol. 168 (2006) 1107-1118

[53] K. Simons, M. J. Gerl, Revitalizing membrane rafts: new tools and insights. Nat. Rev. Mol. Cell Biol. 11 (2010) 688-699.

[54] D. Calay, D. Vind-Kezunovic, A. Frankart, S. Lambert, Y. Poumay, R. Gniadecki, Inhibition of Akt signaling by exclusion from lipid rafts in normal and transformed epidermal keratinocytes. J. Invest. Dermatol. 130 (2010) 1136-1145.

[55] M. Reis-Sobreiro, G Roué, A. Moros, C. Gajate, J. de la Iglesia-Vicente, D. Colomer, F. Mollinedo, Lipid raft-mediated Akt signaling as a therapeutic target in mantle cell lymphoma. Blood Cancer J. 3 (2013) e118.

[56] H. Y. Oh, J. Leem, S. J. Yoon, S. Yoon, S. J. Hong, Lipid raft cholesterol and genistein inhibit the cell viability of prostate cancer cells via the partial contribution of EGFR-Akt/p70S6k pathway and down-regulation of androgen receptor. Biochem. Biophys. Res. Commun. 393 (2010) 319-324.

[57] Wang, Yan, et al., Caveolin-1 enhances RANKL-induced gastric cancer cell migration. Oncology reports 40.3 (2018): 1287-1296.

[58] Liu, Yuan et al., Lipid rafts promote liver cancer cell proliferation and migration by up-regulation of TLR7 expression. Oncotarget vol. 7, 39 (2016): 63856-63869.

[59] Moreno-Altamirano, M. Maximina Bertha, Israel Aguilar-Carmona, and F. Javier Sanchez-Garcia, Expression of GM1, a marker of lipid rafts, defines two subsets of human monocytes with differential endocytic capacity and lipopolysaccharide responsiveness. Immunology 120.4 (2007): 536-543.

[60] Li, Guanying, et al., Patching of Lipid Rafts by Molecular Self-Assembled Nanofibrils Suppresses Cancer Cell Migration. Chem 2.2 (2017): 283-298.

[61] Gueron, Geraldine, et al. "Critical role of endogenous heme oxygenase 1 as a tuner of the invasive potential of prostate cancer cells." Molecular cancer research (2009): 1541-7786.

[62] Xue, J., et al., Expression of caveolin-1 in tongue squamous cell carcinoma by quantum dots. European journal of histochemistry: EJH 54.2 (2010)

[63] Song, Libing, et al., Flotillin-1 promotes tumor necrosis factor-α receptor signaling and activation of NF-κB in esophageal squamous cell carcinoma cells. Gastroenterology 143.4 (2012): 995-1005.

[64] Wen, Qiuyuan, et al., Flot-2 expression correlates with EGFR levels and poor prognosis in surgically resected non-small cell lung cancer. PloS one 10.7 (2015): e0132190.

[65] Yoo, Seong-Ho, et al., Expression of caveolin-1 is associated with poor prognosis of patients with squamous cell carcinoma of the lung. Lung cancer 42.2 (2003): 195-202.

[66] Krengel, Ute, and Paula A. Bousquet, Molecular recognition of gangliosides and their potential for cancer immunotherapies. Frontiers in immunology 5 (2014): 325.

[67] De Toni, Luca, et al., Gangliosides act as onconeural antigens in paraneoplastic neuropathies. Journal of neuroimmunology 156.1-2 (2004): 178-187.

[68] Ho, Chao-Chi, et al., Up-regulated caveolin-1 accentuates the metastasis capability of lung adenocarcinoma by inducing filopodia formation. The American journal of pathology 161.5 (2002): 1647-1656.

[69] Zhang, Peng-Fei, et al., Identification of flotillin-1 as a novel biomarker for lymph node metastasis and prognosis of lung adenocarcinoma by quantitative plasma membrane proteome analysis. Journal of proteomics 77 (2012): 202-214.

[70] Tanase, Cristiana Pistol, et al., Caveolin-1 overexpression correlates with tumour progression markers in pancreatic ductal adenocarcinoma. Journal of molecular histology 40.1 (2009): 23-29.

[71] Suzuoki, M., et al., Impact of caveolin-1 expression on prognosis of pancreatic ductal adenocarcinoma. British Journal of Cancer 87.10 (2002): 1140.

[72] Fecchi, Katia, et al., Human melanoma cells express FGFR/Src/Rho signaling that entails an adhesion-independent caveolin-1 membrane association. International journal of cancer 130.6 (2012): 1273-1283.

[73] Hazarika, Parul, et al., Up-regulation of Flotillin-2 is associated with melanoma progression and modulates expression of the thrombin receptor protease activated receptor 1. Cancer research 64.20 (2004): 7361-7369.

[74] Doherty, Sean D., et al., High flotillin-2 expression is associated with lymph node metastasis and Breslow depth in melanoma. Melanoma research 16.5 (2006): 461-463.

[75] Raimondo, Francesca, et al., Caveolin-1 and flotillin-1 differential expression in clinical samples of renal cell carcinoma. The Open Proteomics J 1 (2008): 87-98.

[76] Fong, Andrew, et al., Expression of caveolin-1 and caveolin-2 in urothelial carcinoma of the urinary bladder correlates with tumor grade and squamous differentiation. American journal of clinical pathology 120.1 (2003): 93-100.

[77] Nimri, Lili, et al., Restoration of caveolin-1 expression suppresses growth, membrane-type-4 metalloproteinase expression and metastasis-associated activities in colon cancer cells. Molecular carcinogenesis 52.11 (2013): 859-870.

[78] Kato, Kentaro, et al., Overexpression of caveolin-1 in esophageal squamous cell carcinoma correlates with lymph node metastasis and pathologic stage. Cancer 94.4 (2002): 929-933.

[79] Ando, Takuya, et al., The overexpression of caveolin-1 and caveolin-2 correlates with a poor prognosis and tumor progression in esophageal squamous cell carcinoma. Oncology reports 18.3 (2007): 601-609.

[80] Huang, Cong-Fa, et al., Prognostic and predictive values of SPP1, PAI and caveolin-1 in patients with oral squamous cell carcinoma. International journal of clinical and experimental pathology 7.9 (2014): 6032-6039.

[81] Zhao, Xuening, et al., Caveolin-1 is overexpressed in hypopharyngeal squamous cell carcinoma and correlates with clinical parameters. Oncology letters 12.4 (2016): 2371-2374.

[82] Liu, Jie, et al., Flotillin-2 promotes metastasis of nasopharyngeal carcinoma by activating NF-κB and PI3K/Akt3 signaling pathways. Scientific reports 5 (2015): 11614.

[83] Gao, Wen, et al., Plasma membrane proteomic analysis of human Gastric Cancer tissues: revealing flotillin 1 as a marker for Gastric Cancer. BMC cancer 15.1 (2015): 367.

[84] Cao, Ke, et al., SiRNA-mediated flotillin-2 (Flot2) downregulation inhibits cell proliferation, migration, and invasion in gastric carcinoma cells. Oncology Research Featuring Preclinical and Clinical Cancer Therapeutics 21.5 (2014): 271-279.

[85] Gao, Yang, et al., High expression of flotillin-1 is associated with lymph node metastasis and poor prognosis in vulvar squamous cell carcinoma. Int J Clin Exp Pathol 9.9 (2016): 9538-9546.

[86] Barresi, V., et al., Caveolin-1 in meningiomas: expression and clinico-pathological correlations. Acta neuropathologica 112.5 (2006): 617-626.

[87] Ferraldeschi, Roberta, et al., PTEN protein loss and clinical outcome from castration-resistant prostate cancer treated with abiraterone acetate. European urology 67.4 (2015): 795-802.

What is claimed is:

1. A method for modulating a lipid raft integrity of a cell, comprising administering a pharmaceutical composition to a subject in need of treatment for modulating the lipid raft integrity, wherein the pharmaceutical composition comprises a benzenesulfonamide derivative that serves as a cholesterol-depleting agent, and a pharmaceutically acceptable excipient thereof, wherein the method treats a disease susceptible to amelioration by a decreased level of the lipid raft integrity, wherein the disease is a cancer, and wherein the cancer expresses lipid raft markers and is at least one selected from the group consisting of prostate cancer, kidney cancer, bladder cancer, seminoma, ovarian cancer, cervical cancer, colon cancer, thyroid cancer, meningiomas, bile duct cancer, and vulvar cancer;

wherein the benzenesulfonamide derivative is para-toluene sulfonamide, and wherein the cancer is screened for increased expression of lipid raft markers.

2. A method for treating cancer, comprising administering a pharmaceutical composition to a subject in need thereof, wherein the pharmaceutical composition comprises a benzenesulfonamide derivative that serves as a cholesterol-depleting agent, and a pharmaceutically acceptable excipient thereof, wherein the cancer is susceptible to amelioration by a decreased level of the lipid raft integrity, and wherein the cancer expresses lipid raft markers and is at least one selected from the group consisting of prostate cancer, kidney cancer, bladder cancer, seminoma, ovarian cancer, cervical cancer, colon cancer, thyroid cancer, meningiomas, bile duct cancer, and vulvar cancer;

wherein the benzenesulfonamide derivative is para-toluene sulfonamide, and wherein the cancer is screened for increased expression of lipid raft markers.

3. The method according to claim 2, further comprising administering at least one additional anti-cancer therapy to the subject.

4. The method according to claim 3, wherein the additional anti-cancer therapy is whole body chemotherapy, radiotherapy, or thermal therapy.

5. The method according to claim 2, wherein the benzenesulfonamide derivative in the pharmaceutical composition is administered to the subject in a therapeutically effective amount of from about 20 mg to about 4000 mg per day.

6. The method according to claim 2, wherein the pharmaceutical composition modulates lipid raft integrity of a cancer cell.

7. The method according to claim 6, wherein the pharmaceutical composition depletes cholesterol from plasma membrane of the cancer cell.

8. The method according to claim 6, wherein the pharmaceutical composition disturbs or disrupts the lipid raft integrity of the cancer cell.

9. A method for treating a subject suffering from prostate cancer, kidney cancer, bladder cancer, seminoma, ovarian cancer, cervical cancer, thyroid cancer, meningiomas, bile duct cancer, or vulvar cancer, the method comprising:

screening prostate cancer, kidney cancer, bladder cancer, seminoma, ovarian cancer, cervical cancer, thyroid cancer, meningiomas, bile duct cancer, or vulvar cancer for increased expression of lipid raft markers; and administering to the subject with prostate cancer, kidney cancer, bladder cancer, seminoma, ovarian cancer, cervical cancer, thyroid cancer, meningiomas, bile duct cancer, or vulvar cancer having increased expression of lipid raft markers an effective amount of a pharmaceutical composition that comprises para-toluene sulfonamide that serves as a cholesterol-depleting agent, and a pharmaceutically acceptable excipient thereof.

10. The method according to claim 9, further comprising administering at least one additional anti-cancer therapy to the subject.

11. The method of claim 9 wherein the subject is suffering from prostate cancer.

* * * * *